(12) United States Patent
Park et al.

(10) Patent No.: US 7,575,818 B2
(45) Date of Patent: Aug. 18, 2009

(54) ORGANIC METAL COMPOUNDS IN WHICH COMPOUNDS FOR HOST AND COMPOUNDS FOR DOPANT ARE CONNECTED, ORGANIC ELECTROLUMINESENCE DISPLAY DEVICES USING THE COMPOUNDS AND METHOD FOR PREPARATION OF THE DEVICES

(75) Inventors: Soo Jin Park, Seoul (KR); Dong Hyun Jung, Suwon-si (KR); Dae Yup Shin, Suwon-si (KR); Byung Doo Chin, Seongnam-si (KR); Tae Hyuk Kwon, Seoul (KR); Myoung Ki Kim, Jechun-si (KR); Jong In Hong, Seoul (KR)

(73) Assignee: Samsung Mobile Display Co., Ltd., Yongin, Gyunggi-Do (KR)

( * ) Notice: Subject to any disclaimer, the term of this patent is extended or adjusted under 35 U.S.C. 154(b) by 483 days.

(21) Appl. No.: 11/364,517

(22) Filed: Feb. 27, 2006

(65) Prior Publication Data

US 2006/0237714 A1 Oct. 26, 2006

(30) Foreign Application Priority Data

Apr. 21, 2005 (KR) .................... 10-2005-0033082

(51) Int. Cl.
*H01L 51/54* (2006.01)
*C09K 11/06* (2006.01)

(52) U.S. Cl. ............. 428/690; 428/917; 313/504; 313/506; 257/40; 257/E51.044; 546/4; 548/440

(58) Field of Classification Search ................ None
See application file for complete search history.

(56) References Cited

U.S. PATENT DOCUMENTS

| | | |
|---|---|---|
| 6,303,238 B1 | 10/2001 | Thompson et al. |
| 2001/0053463 A1 | 12/2001 | Thompson et al. |
| 2002/0034656 A1 | 3/2002 | Thompson et al. |
| 2002/0121638 A1 | 9/2002 | Grushin et al. |
| 2004/0086742 A1* | 5/2004 | Ma et al. ............... 428/690 |
| 2004/0219387 A1* | 11/2004 | Li et al. ............... 428/690 |

FOREIGN PATENT DOCUMENTS

WO WO 03/079736 A1 * 9/2003

* cited by examiner

*Primary Examiner*—Marie R. Yamnitzky
(74) *Attorney, Agent, or Firm*—Knobbe Martens Olson & Bear LLP

(57) ABSTRACT

Provided are organic metal compounds in which compounds for host and compounds for dopant are connected, organic electroluminescence display devices using the compounds and a method for preparation of the devices. Also provided are organic metal compounds in which compounds for host and compounds for dopant where connected to make energy transmission between host and dopant possible at a molecular level, an organic electroluminescence display device using the same and a preparation method thereof.

7 Claims, 4 Drawing Sheets

ORGANIC METAL COMPOUNDS IN WHICH COMPOUNDS FOR HOST AND COMPOUNDS FOR DOPANT ARE CONNECTED, ORGANIC ELECTROLUMINESENCE DISPLAY DEVICES USING THE COMPOUNDS AND METHOD FOR PREPARATION OF THE DEVICES

CROSS-REFERENCE TO RELATED APPLICATIONS

This application claims the benefit of Korean Patent Application No. 10-2005-0033082, filed on Apr. 21, 2005, in the Korean Intellectual Property Office, the disclosure of which is incorporated herein by reference.

BACKGROUND OF THE INVENTION

1. Field of the Invention

The present embodiments relate to organic metal compounds in which compounds for host and compounds for dopant are connected, organic electroluminescence display devices using the compounds and a method for preparation of the devices. More precisely, the present embodiments relate to organic metal compounds in which compounds for host and compounds for dopant are connected to make energy transmission between host and dopant possible on a molecular level, organic electroluminescence display devices using the same and a preparation method thereof.

2. Description of the Related Art

As a self-emissive display device, an electroluminescence display device (EL device) has a broad visual angle, excellent contrast, and a quick response time.

EL devices are divided into inorganic EL devices and organic EL devices according to the emitting layer forming materials. Organic EL devices have advantages over inorganic EL devices such as increased brightness and driving voltage, a quick response time, and polychromy.

In general, in the structure of an organic EL device, anodes formed on the substrate, and in the upper part of the anode, hole transport layer, emitting layer, electron transport layer and cathode are formed in that order. The hole transport layer, the emitting layer, and the electron transport layer are organic thin films composed of organic compounds.

The drive principal of organic EL devices having the above structure is as follows.

Once voltage is impressed between the anode and cathode, holes are infused from the anode into the emitting layer via the hole transport layer. In the meantime, electrons are infused into the emitting layer from the cathode via the electron transport layer. In the region of the emitting layer, carriers are rearranged to form exitons. The excited exiton is transformed into ground state, resulting in emission of the emitting layer molecules. As a result, images are formed. Emitting materials are classified according to emitting mechanism into two groups; one is composed of fluorescent materials using exitons in the state of a singlet, and the other group is composed of phosphorescent substances using exitons in the state of a triplet.

Phosphorescent substances have an organomineral compound structure containing generally heavy atoms, by which an exiton can be transformed from the state of triplet, a forbidden transition, through allowed transition. Phosphorescent substances have much higher emitting efficiency by using triplet exitons having 75% generation ratio than fluorescent materials which use singlet exitons with 25% generation ratio.

Emitting layers formed by phosphorescent substances are composed of a host material and a dopant material which is luminous by energy transmission from the host material. Dopant materials include various iridium metal compounds. As a part of a study on organic electroluminescent materials using iridium compounds, research teams at Princeton University and the University of Southern California reported phosphorescent substances based on iridium, and platinum metal compounds. But more studies are ongoing to develop a better stable luminous material.

While a low molecular weight organic EL material forms a device by primarily using a dry process such as vacuum deposition, a high molecular weight EL material forms a device by using a wet process such as spin coating, etc. The low molecular weight EL material cannot compose a device by a wet process because of its low solubility. Although the high molecular weight EL material has a high enough solubility to form a device by a wet process, it has a low emission property, in particular, shorter life time than the low molecular EL material. Thus, an organic EL material is need which has a high solubility and can form a device by a wet process, an easier and more economical process than deposition, and at the same time has emission properties as high as a low molecular EL material.

SUMMARY OF THE INVENTION

It is an object of the present embodiments to provide an organic metal compound in which compounds for host and compounds for dopant are connected.

It is another object of the present embodiments to provide an organic electroluminescence device using the organic metal compound in which compounds for host and compounds for dopant are connected.

It is a further object of the present embodiments to provide a preparation method of the organic electroluminescence device using the organic metal compound in which compounds for host and compounds for dopant are connected.

In order to achieve the first object of the embodiments, the present embodiments provide an organic metal compound in which compounds for dopant are connected by a linker to compounds for host having the same or different energy gap.

The present embodiments also provide the organic metal compound, represented by the following formula 1, in which compounds for host and compounds for dopant are connected by a linker.

Formula 1

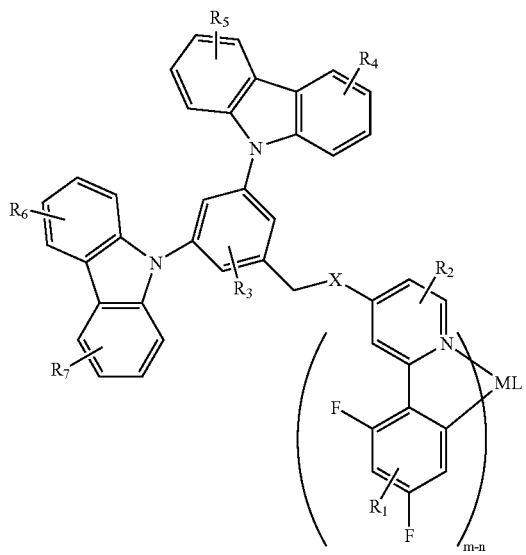

wherein,

X can have the following structures;

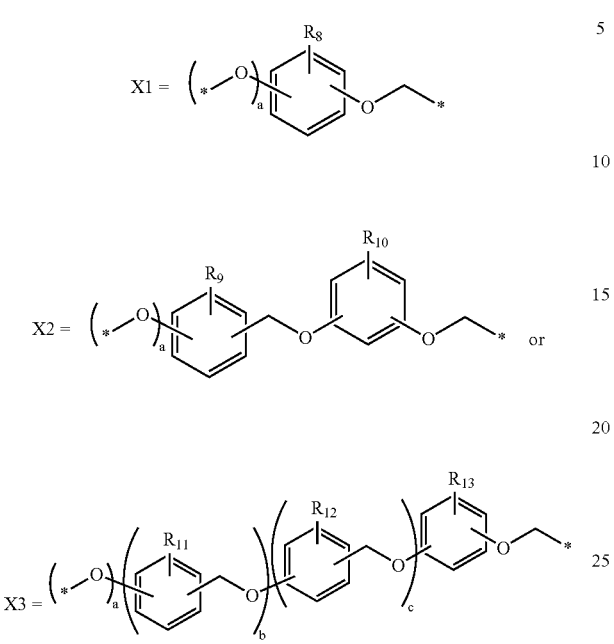

R$_1$-R$_{13}$ are independently mono-substituted or multi-substituted functional groups selected from the group consisting of H, cyano, hydroxy, thiol, halogen atoms, substituted or nonsubstituted C$_1$-C$_{30}$ alkyl, substituted or nonsubstituted C$_1$-C$_{30}$ alkoxy, substituted or nonsubstituted C$_2$-C$_{30}$ alkenyl, substituted or nonsubstituted C$_6$-C$_{30}$ aryl, substituted or nonsubstituted C$_6$-C$_{30}$ arylalkyl, substituted or nonsubstituted C$_6$-C$_{30}$ aryloxy, substituted or nonsubstituted C$_2$-C$_{30}$ heteroaryl, substituted or nonsubstituted C$_2$-C$_{30}$ heteroarylalkyl, substituted or nonsubstituted C$_2$-C$_{30}$ heteroaryloxy, substituted or nonsubstituted C$_5$-C$_{30}$ cycloalkyl, substituted or nonsubstituted C$_2$-C$_{30}$ heterocycloalkyl, substituted or nonsubstituted C$_1$-C$_{30}$ alkylcarbonyl, substituted or nonsubstituted C$_7$-C$_{30}$ arylcarbonyl, C$_1$-C$_{30}$ alkylthiol, —Si(Z')(Z'')(Z''') (wherein Z', Z'' and Z''' are independently H or C$_1$-C$_{30}$ alkyl), or —N(Z')(Z'') (wherein Z' and Z'' are independently H or C$_1$-C$_{30}$ alkyl), and the neighboring groups among functional groups of R$_1$-R$_{13}$ can be linked to each other to form a ring;

a, b and c are independently an integer of 1, 2, or 3;

M can be Ir, Os, Pt, Pb, Re or Ru; and

L can be a bidentate ligand, m is 3, and n is 1 or 2.

In order to achieve the second object of the embodiments, the present embodiments provide an organic electroluminescence device comprised of an organic layer between a pair of electrodes that contains organic metal compound in which compounds for host and compounds for dopant are connected.

In one embodiment, there is provided an organic metal compound represented by formula 1, wherein the compounds for host and the compounds for dopant have the same or a different energy gap between their HOMO and LUMO and are connected by a linker.

Formula 1

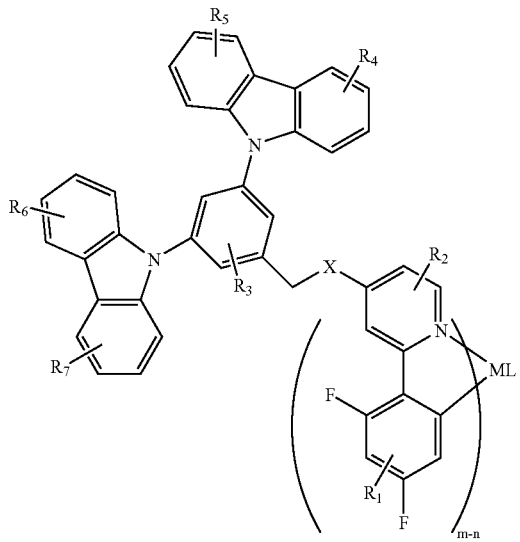

wherein,

X has one of the following structures;

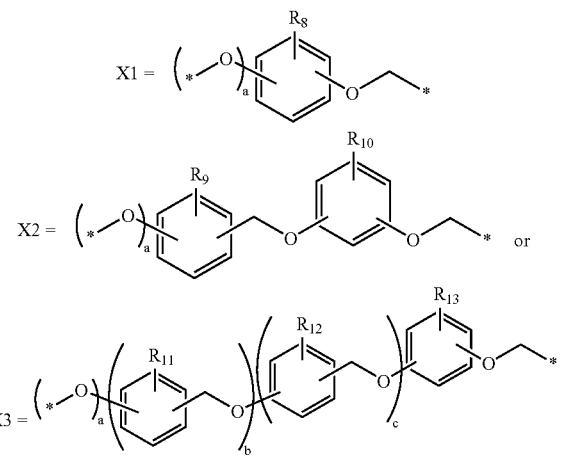

wherein R$_1$-R$_{13}$ are independently mono-substituted or multi-substituted functional groups selected from the group consisting of H, cyano, hydroxy, thiol, halogen atoms, substituted or nonsubstituted C$_1$-C$_{30}$ alkyl, substituted or nonsubstituted C$_1$-C$_{30}$ alkoxy, substituted or nonsubstituted C$_2$-C$_{30}$ alkenyl, substituted or nonsubstituted C$_6$-C$_{30}$ aryl, substituted or nonsubstituted C$_6$-C$_{30}$ arylalkyl, substituted or nonsubstituted C$_6$-C$_{30}$ aryloxy, substituted or nonsubstituted C$_2$-C$_{30}$ heteroaryl, substituted or nonsubstituted C$_2$-C$_{30}$ heteroarylalkyl, substituted or nonsubstituted C$_2$-C$_{30}$ heteroaryloxy, substituted or nonsubstituted C$_5$-C$_{30}$ cycloalkyl, substituted or nonsubstituted C$_2$-C$_{30}$ heterocycloalkyl, substituted or nonsubstituted C$_1$-C$_{30}$ alkylcarbonyl, substituted or nonsubstituted C$_7$-C$_{30}$ arylcarbonyl, C$_1$-C$_{30}$ alkylthiol, —Si(Z')(Z'')(Z''') (wherein Z', Z'' and Z''' are independently H or C$_1$-C$_{30}$ alkyl), and —N(Z')(Z'') (wherein Z' and Z'' are independently H or C$_1$-C$_{30}$ alkyl), and wherein the neighboring groups among functional groups of $R_1$- $R_{13}$ can be linked to each other to form a ring;

a, b and c are independently 1, 2 or 3;

M is selected from the group consisting of Ir, Os, Pt, Pb, Re and Ru; and

L is a bidentate ligand, m is 3, and n is 1 or 2.

In order to achieve the third object of the embodiments, the present embodiments provide a preparation method of an organic electroluminescence device comprising the steps of forming the first electrode on substrate; forming an organic layer on the first electrode; and forming the second electrode on the organic layer, wherein the organic layer is formed by doping the organic metal compound in which compounds for host and compounds for dopant are connected

BRIEF DESCRIPTION OF THE DRAWINGS

These and/or other aspects and advantages of the embodiments will become apparent and more readily appreciated from the following description of the preferred embodiments, taken in conjunction with the accompanying drawings of which.

DETAILED DESCRIPTION OF PREFERRED EMBODIMENTS

Figure 1:
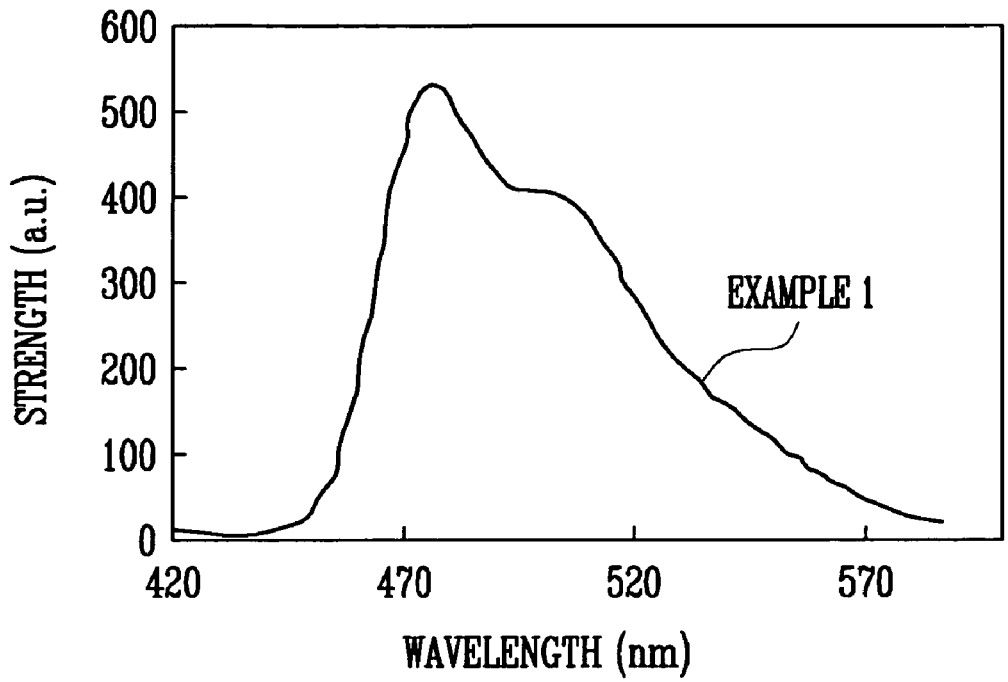
FIG. 1 is a graph showing a PL (photoluminescence) spectrum in chloroform solution of the compound represented by formula 6, synthesized in Example 1.

Hereinafter, preferred embodiments will be described with reference to the accompanying drawings, wherein the preferred embodiments are provided to be readily understood by those skilled in the art.

The organic metal compound of the present embodiments is prepared by connecting compounds for dopant with compounds for host having the same or different energy gap between their HOMO (highest occupied molecular orbital)-LUMO (lowest unoccupied molecular orbital). The energy gap of compounds for host can be bigger than that of compounds for dopant or the energy gap of compounds for dopant can be bigger than that of compounds for host. The preferred energy gap between compounds for host and compounds for dopant is about 0 to about 400 nm, which has been found to enable energy transmission between a host and a dopant in the same molecule as well as the increase of emission efficiency.

The resultant organic metal compound in which compounds for host and compounds for dopant are connected not only shows excellent emission properties but also increases the molecular weight, resulting in enhanced solubility.

The organic metal compound of the present embodiments has a structure in which compounds for host and compounds for dopant are connected by a linker. And several compounds for host can be connected to a compound for dopant according to the kinds of linkers used.

The linker should be a moiety capable of breaking p conjugation between compounds for host and compounds for dopant, and should preferably be a moiety having a multifunctional group which does not disturb energy transmission between a host and a dopant. For example, a moiety containing one or more oxygen atoms is preferred.

For example, hydroquinone, 3,5-dihydroxybenzylalcohol, etc, can be used as a linker.

As explained above, the number of compounds for host to be connected to a compound for dopant is regulated by a linker, possibly leading to the regulation of doping concentration for organic electroluminescence device.

More specifically, it is preferred for a connecter to have one of the following structures:

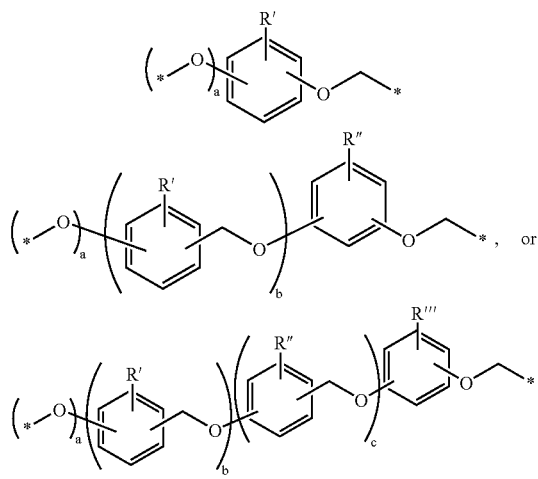

wherein R', R" and R''' are independently mono-substituted or multi-substituted functional groups selected from the group consisting of H; cyano, hydroxy, thiol, halogen atoms, substituted or nonsubstituted $C_1$-$C_{30}$ alkyl, substituted or nonsubstituted $C_1$-$C_{30}$ alkoxy, substituted or nonsubstituted $C_2$-$C_{30}$ alkenyl, substituted or nonsubstituted $C_6$-$C_{30}$ aryl, substituted or nonsubstituted $C_6$-$C_{30}$ arylalkyl, substituted or nonsubstituted $C_6$-$C_{30}$ aryloxy, substituted or nonsubstituted $C_2$-$C_{30}$ heteroaryl, substituted or nonsubstituted $C_2$-$C_{30}$ heteroarylalkyl, substituted or nonsubstituted $C_2$-$C_{30}$ heteroaryloxy, substituted or nonsubstituted $C_5$-$C_{30}$ cycloalkyl, substituted or nonsubstituted $C_2$-$C_{30}$ heterocycloalkyl, substituted or nonsubstituted $C_1$-$C_{30}$ alkylcarbonyl, substituted or nonsubstituted $C_7$-$C_{30}$ arylcarbonyl, $C_1$-$C_{30}$ alkylthiol, —Si(Z')(Z")(Z''') (wherein Z', Z", and Z''' are independently H or $C_1$-$C_{30}$ alkyl), or —N(Z')(Z")(wherein Z' and Z" are independently H or $C_1$-$C_{30}$ alkyl), and the neighboring groups among functional groups of R'-R" can be linked to each other to form a ring.

A compound having one of the following structures can be used as a compound for the host:

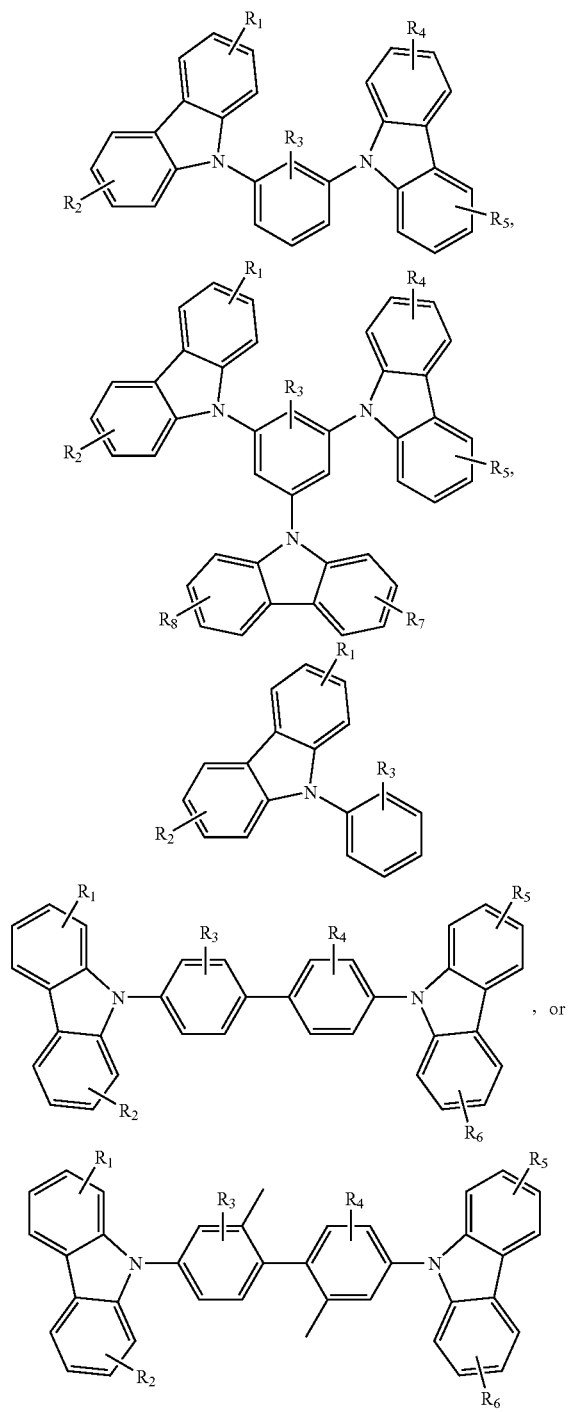

wherein $R_1$-$R_7$ are independently mono-substituted or multi-substituted functional groups selected from the group consisting of H, cyano, hydroxy, thiol, halogen atoms, substituted or nonsubstituted $C_1$-$C_{30}$ alkyl, substituted or nonsubstituted $C_1$-$C_{30}$ alkoxy, substituted or nonsubstituted $C_2$-$C_{30}$ alkenyl, substituted or nonsubstituted $C_6$-$C_{30}$ aryl, substituted or nonsubstituted $C_6$-$C_{30}$ arylalkyl, substituted or nonsubstituted $C_6$-$C_{30}$ aryloxy, substituted or nonsubstituted $C_2$-$C_{30}$ heteroaryl, substituted or nonsubstituted $C_2$-$C_{30}$ heteroarylalkyl, substituted or nonsubstituted $C_2$-$C_{30}$ heteroaryloxy, substituted or nonsubstituted $C_5$-$C_{30}$ cycloalkyl, substituted or nonsubstituted $C_2$-$C_{30}$ heterocycloalkyl, substituted or nonsubstituted $C_1$-$C_{30}$ alkylcarbonyl, substituted or nonsubstituted $C_7$-$C_{30}$ arylcarbonyl, $C_1$-$C_{30}$ alkylthiol, —Si(Z')(Z'')(Z''')(wherein Z', Z'' and Z''' are independently H or $C_1$-$C_{30}$ alkyl), or —N(Z')(Z'')(wherein Z' and Z'' are independently H or $C_1$-$C_{30}$ alkyl), and the neighboring groups among functional groups of $R_1$- $R_7$ can be linked to each other to form a ring.

A compound having the following structure or its derivatives can be used as a compound for dopant:

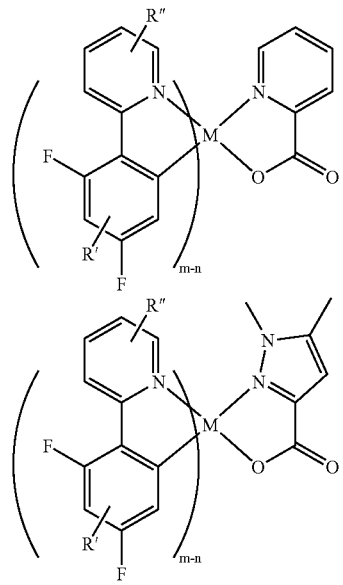

wherein R' and R" are independently mono-substituted or multi-substituted functional groups selected from the group consisting of H, cyano, hydroxyl, thiol, halogen atoms, substituted or nonsubstituted $C_1$-$C_{30}$ alkyl, substituted or nonsubstituted $C_1$-$C_{30}$ alkoxy, substituted or nonsubstituted $C_2$-$C_{30}$ alkenyl, substituted or nonsubstituted $C_6$-$C_{30}$ aryl, substituted or nonsubstituted $C_6$-$C_{30}$ arylalkyl, substituted or nonsubstituted $C_6$-$C_{30}$ aryloxy, substituted or nonsubstituted $C_2$-$C_{30}$ heteroaryl, substituted or nonsubstituted $C_2$-$C_{30}$ heteroarylalkyl, substituted or nonsubstituted $C_2$-$C_{30}$ heteroaryloxy, substituted or nonsubstituted $C_5$-$C_{30}$ cycloalkyl, substituted or nonsubstituted $C_2$-$C_{30}$ heterocycloalkyl, substituted or nonsubstituted $C_1$-$C_{30}$ alkylcarbonyl, substituted or nonsubstituted $C_7$-$C_{30}$ arylcarbonyl, $C_1$-$C_{30}$ alkylthiol, —Si(Z')(Z'')(Z''')(wherein Z', Z'' and Z''' are independently H or $C_1$-$C_{30}$ alkyl), or —N(Z')(Z'')(wherein Z' and Z'' are independently H or $C_1$-$C_{30}$ alkyl); M is Ir, Os, Pt, Pb, Re or Ru; m is 3; and n is 1 or 2.

In a preferable embodiment of the organic metal compound in which compounds for host and compounds for dopant are connected, a compound represented by the following formula 1, which has good emission properties and is available as a coloring material for a display device is prepared.

Formula 1

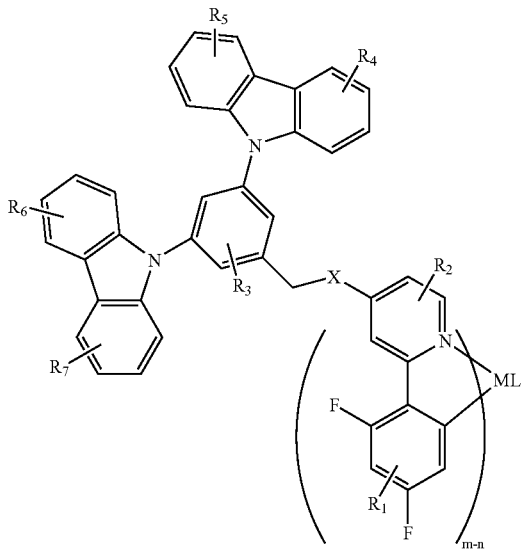

wherein,
X can have the following structures;

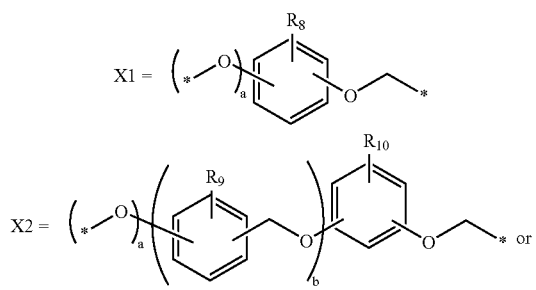

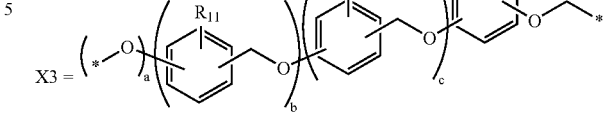

$R_1$- $R_{13}$ are independently mono-substituted or multi-substituted functional groups selected from the group consisting of H, cyano, hydroxy, thiol, halogen atoms, substituted or nonsubstituted $C_1$-$C_{30}$ alkyl, substituted or nonsubstituted $C_1$-$C_{30}$ alkoxy, substituted or nonsubstituted $C_2$-$C_{30}$ alkenyl, substituted or nonsubstituted $C_6$-$C_{30}$ aryl, substituted or nonsubstituted $C_6$-$C_{30}$ arylalkyl, substituted or nonsubstituted $C_6$-$C_{30}$ aryloxy, substituted or nonsubstituted $C_2$-$C_{30}$ heteroaryl, substituted or nonsubstituted $C_2$-$C_{30}$ heteroarylalkyl, substituted or nonsubstituted $C_2$-$C_{30}$ heteroaryloxy, substituted or nonsubstituted $C_5$-$C_{30}$ cycloalkyl, substituted or nonsubstituted $C_2$-$C_{30}$ heterocycloalkyl, substituted or nonsubstituted $C_1$-$C_{30}$ alkylcarbonyl, substituted or nonsubstituted $C_7$-$C_{30}$ arylcarbonyl, $C_1$-$C_{30}$ alkylthiol, —Si(Z')(Z'')(Z''')(wherein Z',Z'' and Z''' are independently H or $C_1$-$C_{30}$ alkyl), or —N(Z')(Z'')(wherein Z' and Z'' are independently H or $C_1$-$C_{30}$ alkyl), and the neighboring groups among functional groups of $R_1$- $R_{13}$ can be linked to each other to form a ring;

a, b and c are independently an integer of 1-3;

M is Ir, Os, Pt, Pb, Re or Ru; and

L is a bidentate ligand, m is 3, and n is 1 or 2.

The compound of the present embodiments, represented by the formula 1, has one or the representative structures of the following formulae 2-4, according to a linker.

The structure 1 is a compound having X1 in the position of X in the above formula 1, which is represented by the below formula 2.

Formula 2

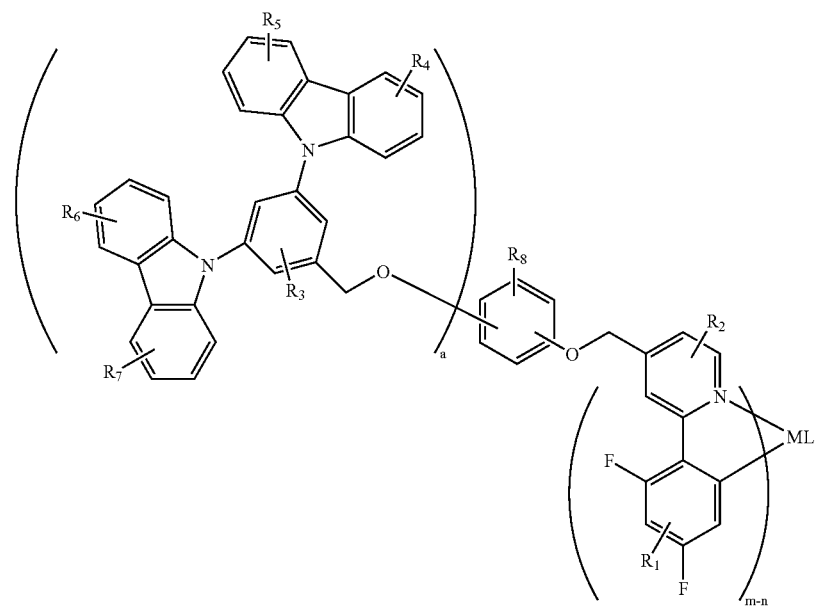

wherein, $R_1$-$R_8$, a, M, L, m, and n are as indicated in the above formula 1.

The structure 2 is a compound having X2 in the position of X in the above formula 1, which is represented by the below formula 3.

wherein, $R_1$- $R_7$, $R_{11}$-$R_{13}$, a, b, c, M, L, m, and n are as indicated in the above formula 1.

In the compound of formula 1 of the present embodiments, L can be one of acetylacetonate(acac), hexafluoroacetylacetonate(hfacac), tetramethylheptanedionate(tmd), diben-

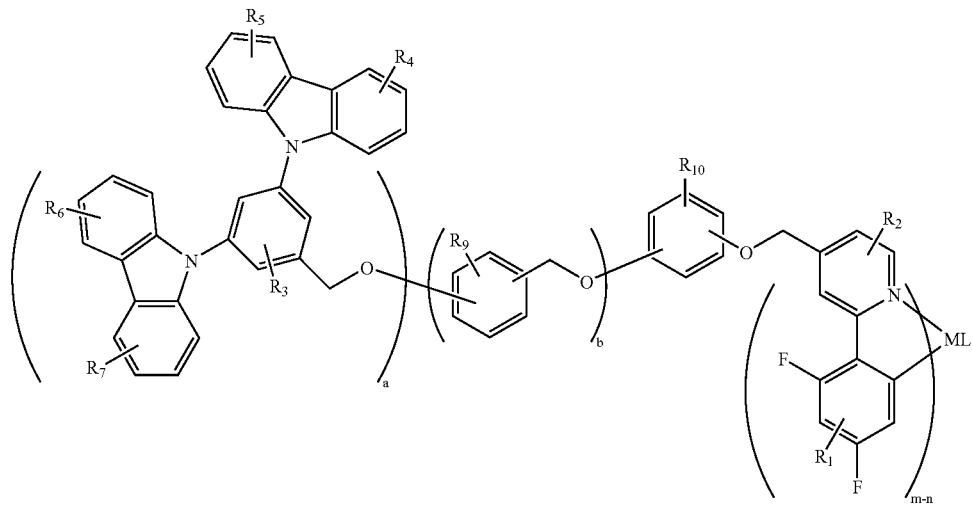

Formula 3 wherein, $R_1$- $R_7$, $R_9$, $R_{10}$, a, b, M, L, m, and n are as indicated in the above formula 1.

The structure 3 is a compound having X3 in the position of X of the above formula 1, which is represented by the below formula 4.

zoylmethane(dbm), picolinate(pic), quinolinecarboxylate (quin), alpha-amino acid L-proline (L-pro), 1-(2-hydroxyphenyl)pyrazolate(oppz), 3-isoquinolinecarboxylate (3iq), phenylpyrazole(ppz), salicylidene(sal),

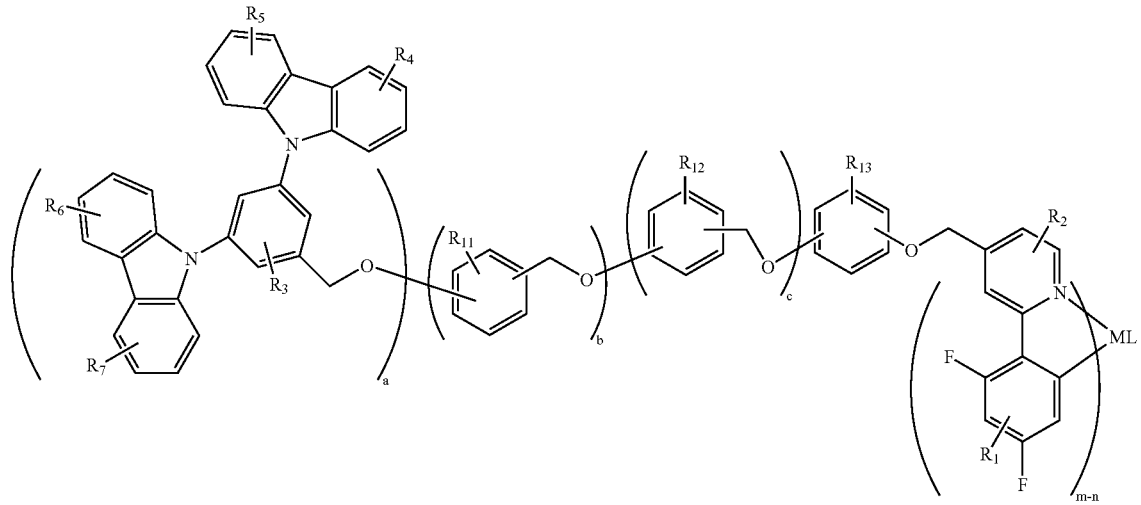

Formula 4

8-hydroxyquinolinate(hquin), 1,5-dimethyl-3-pyrazolecarboxylate(dm3PC), etc, represented by the following structures, but not limited thereto acac
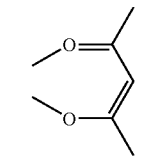

hfacac
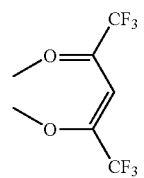

tmd
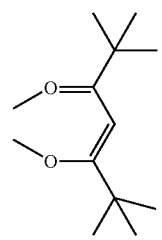

dbm
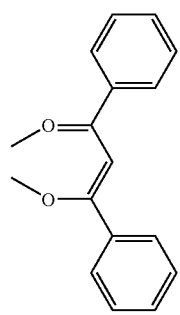

pic
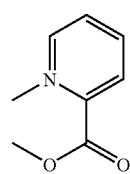

quin
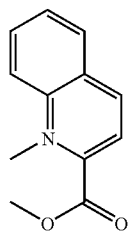

L-pro
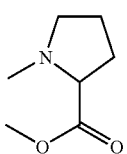

-continued oppz
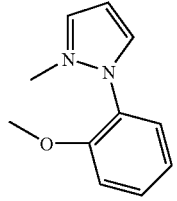

3iq
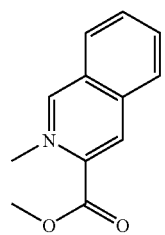

ppz
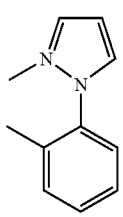

sal
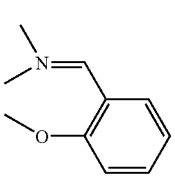

hquin
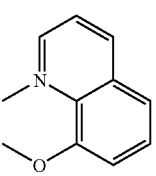

dm3PC
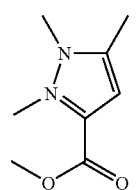

The preferred structure 1 of the compound of the above formula 1 of the present embodiments can include organic metal compounds represented by the following formulae 6-9, in which X is X1, M is Ir, $R_1$ is H or cyano, $R_2$-$R_8$ are H, a is 1, m and n are 2, and L is picolinate or 1,5-dimethyl-3-pyrazolecarboxylate.

Formula 6
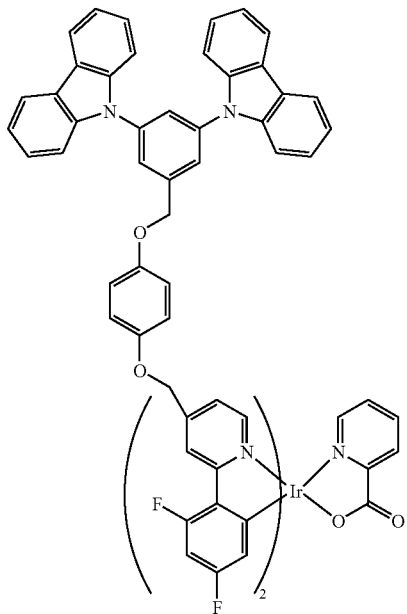
Formula 7
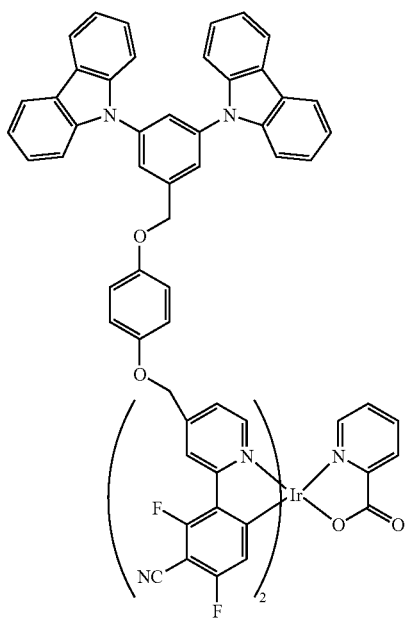
Formula 8
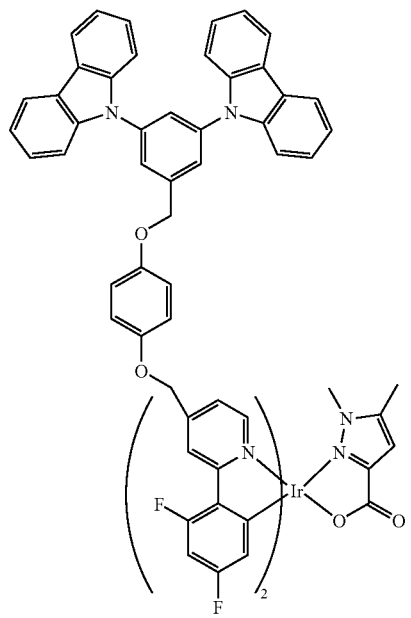
Formula 9
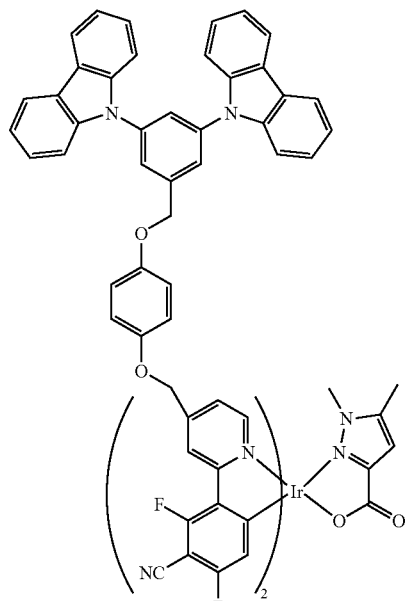
The preferred structure 2 of the compound of the above formula 1 of the present embodiments can include organic metal compounds represented by the following formulae 10-11, which X is X2, M is Ir, $R_1$ is H or cyano, $R_2$-$R_7$ and $R_9$-$R_{10}$ are H, a is 2, b is 1, m and n are 2, and L is picolinate.

Formula 10
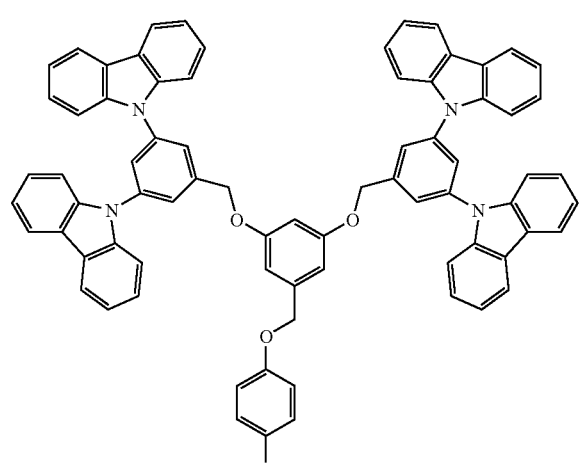
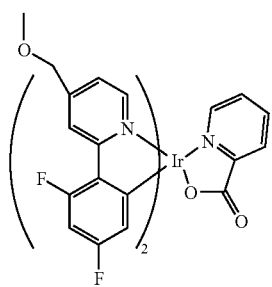
Formula 11
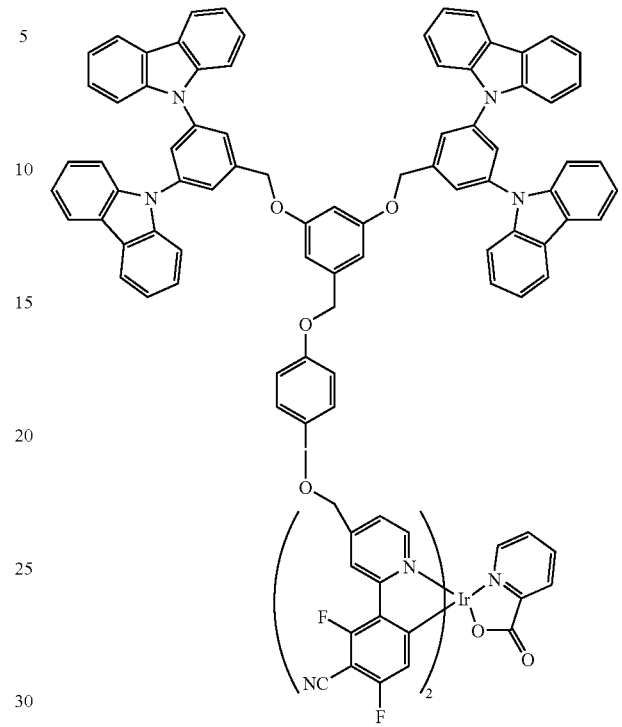
The preferred structure 3 of the compound of the above formula 1 of the present embodiments can include organic metal compounds represented by the following formulae 12-13, in which X is X3, M is Ir, $R_1$ is H or cyano, $R_2$-$R_7$ and $R_{11}$-$R_{13}$ are H, a is 2, b is 2, c is 1, m-n are 2, and L is picolinate.
Formula 12
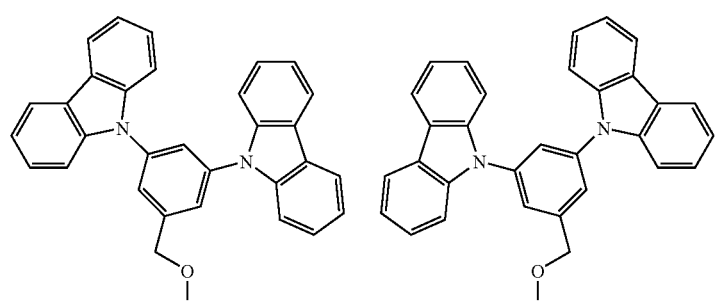

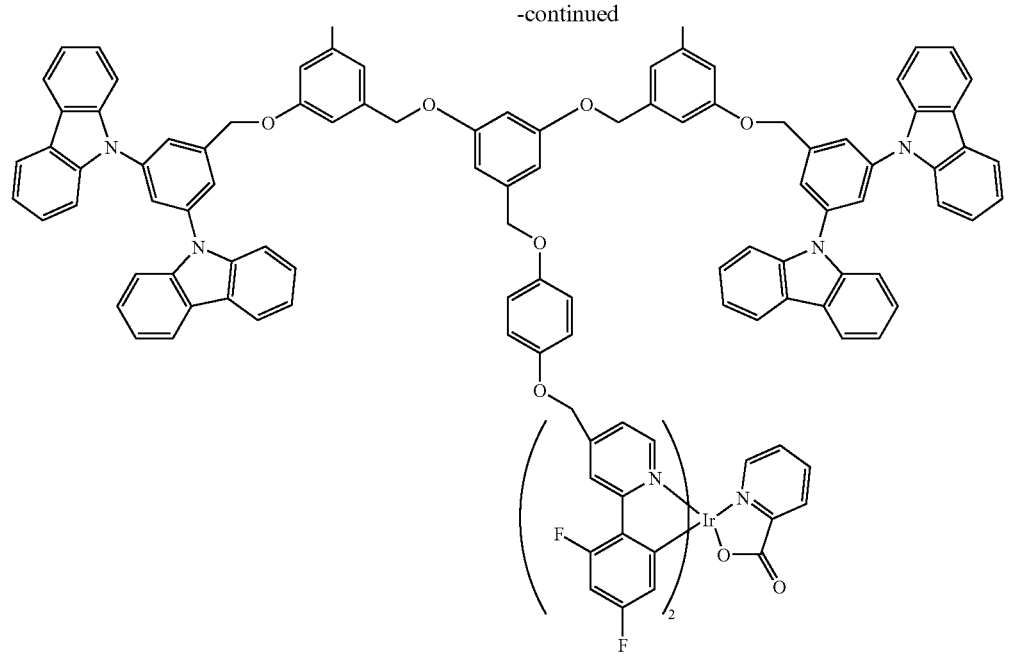
-continued
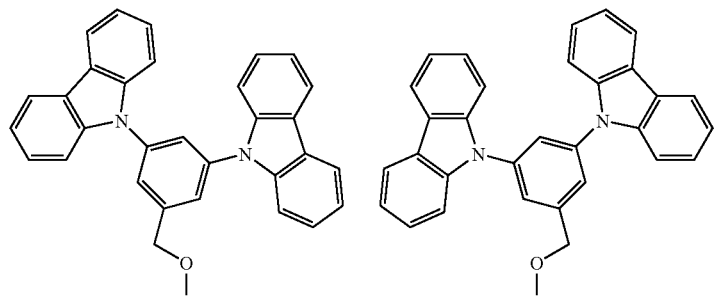
Formula 13
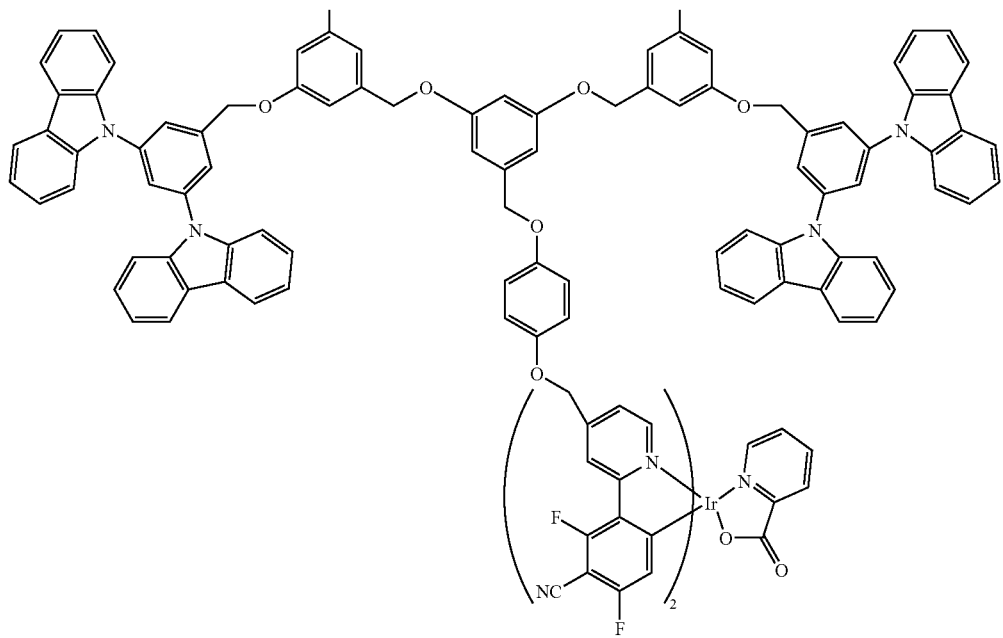

wherein, "nonsubstituted alkyl" or "nonsubstituted alkoxy" means an alkyl having 1-30 carbons in the alkyl part (for example, methyl, ethyl, propyl, butyl, pentyl, hexyl, octyl, nonyl, decyl, undecyl, dodecyl, tridecyl, tetradecyl, pentadecyl, etc, or their isomers), and "substituted alkyl" or "substituted alkoxy" means that at least one hydrogen atom of the nonsubstituted alkyl part is replaced with a halogen atom, hydroxy, nitro, cyano, amino, amidino, hydrazine, hydrazone, carboxyl or its salt, sulfonic acid or its salt, phosphoric acid or its salt, $C_1$-$C_{30}$ alkyl, $C_2$-$C_{30}$ alkenyl, $C_2$-$C_{30}$ alkynyl, $C_6$-$C_{30}$ aryl, $C_7$-$C_{30}$ arylalkyl, $C_2$-$C_{20}$ heteroaryl, or $C_3$-$C_{30}$ heteroalkyl.

"Nonsubstituted alkenyl" means a $C_2$-$C_{30}$ alkenyl which has at least one double bond (for example, ethene, protene, butene, pentene, hexene, etc, or their isomers), and "substituted alkenyl" indicates that at least one hydrogen atom of the nonsubstituted alkenyl above is replaced with one substituent selected from the same list as described above in the case of "substituted alkyl".

"Nonsubstituted aryl" indicates an aromatic carbon ring having 6-30 carbons, forming one or more rings singly or together. The rings can be attached or fused together by pendant method. "Substituted aryl" indicates that at least one hydrogen atom of the nonsubstituted aryl is replaced with one substituent selected from the same list as described above in the case of "substituted alkyl".

"Nonsubstituted arylalkyl" indicates that at least one hydrogen atom of the aryl portion of the molecule is replaced with a lower alkyl such as methyl, ethyl, propyl, etc. "Substituted arylalkyl" indicates that at least one hydrogen atom of the nonsubstituted arylalkyl is replaced with one substituent selected from the same list as described above in the case of "substituted alkyl".

"Nonsubstituted aryloxy" indicates that at least one hydrogen atom of aryl portion of the molecular is replaced with oxygen, which is exemplified by phenyloxy, naphthyleneoxy, diphenyloxy, etc. "Substituted aryloxy" indicates that at least one of hydrogen atoms of the nonsubstituted aryloxy is replaced with one substituent selected from the same list as described above in the case of "substituted alkyl".

"Nonsubstituted heteroaryl" means a univalent monocyclic organic compound or a bicyclic aromatic bivalent organic compound with 2-30 cyclic atoms that contains 1, 2 or 3 hetero atoms selected from the group consisting of N, O, P and S, and the remaining cyclic atom therein is C, which is exemplified by thienyl, pyridyl, furyl, etc. "Substituted heteroaryl" indicates that at least one hydrogen atom of the nonsubstituted heteroaryl is replaced with one substituent selected from the same list as described above in the case of "substituted alkyl".

"Nonsubstituted heteroarylalkyl" indicates that at least one hydrogen atom of the heteroaryl portion of the molecule is replaced with a lower alkyl, and "substituted heteroarylalkyl" indicates that at least one hydrogen atom of nonsubstituted heteroarylalkyl is replaced with one substituent selected from the same list as described above in the case of "substituted alkyl".

"Nonsubstituted heteroaryloxy" indicates a molecule in which oxygen is bound to a heteroaryl. "Substituted heteroaryloxy" indicates that at least of hydrogen atom of the nonsubstituted heteroaryloxy is replaced with one substituent selected from the same list as described above in the case of "substituted alkyl".

"Nonsubstituted cycloalkyl" means a univalent monocyclic molecule having 4-30 carbons, which is exemplified by cyclohexyl, cyclopentyl, etc. "Substituted cycloalkyl" indicates that at least one hydrogen atom of nonsubstituted cycloalkyl is replaced with one substituent selected from the same list as described above in the case of "substituted alkyl".

"Nonsubstituted heterocycloalkyl" means a univalent monocyclic molecule having 1-30 cyclic atoms, which contains 1, 2, or 3 heteroatoms selected from the group consisting of N, O, P, or S, and the remaining cyclic atom therein is C, and at least one hydrogen atom is replaced with a lower alkyl. "Substituted heterocycloalkyl" indicates that at least one hydrogen atom of the nonsubstituted heterocycloalkyl is replaced with one substituent selected from the same list as described above in the case of "substituted alkyl".

"Nonsubstituted alkylcarbonyl" is exemplified by acetyl, ethylcarbonyl, isopropylcarbonyl, phenylcarbonyl, naphthalenecarbonyl, diphenylcarbonyl, cyclohexylcarbonyl, etc. "Substituted alkylcarbonyl" indicates that at least one hydrogen atom of the nonsubstituted alkylcarbonyl is replaced with one substituent selected from the same list as described above in the case of "substituted alkyl".

"Nonsubstituted arylcarbonyl" is exemplified by phenylcarbonyl, naphthalenecarbonyl, diphenylcarbonyl, etc. "Substituted arylcarbonyl" indicates that at least one hydrogen atom of the nonsubstituted arylcarbonyl is replaced with one substituent selected from the same list as described above in the case of "substituted alkyl".

The organic metal compound of the present embodiments, represented by formula 1, shows excellent energy transfer resulting from the connecting structure of compounds for host and compounds for dopant having the same or different energy gap, respectively, and increased emission efficiency, as well as increased solubility owing to the increased molecular weight resulted from the connection.

The structure and a preparation method of an organic electroluminescence device using the organic metal compound of the present embodiments in which compounds for host and compounds for dopant are connected are described in detail hereinafter.

Figure 7:
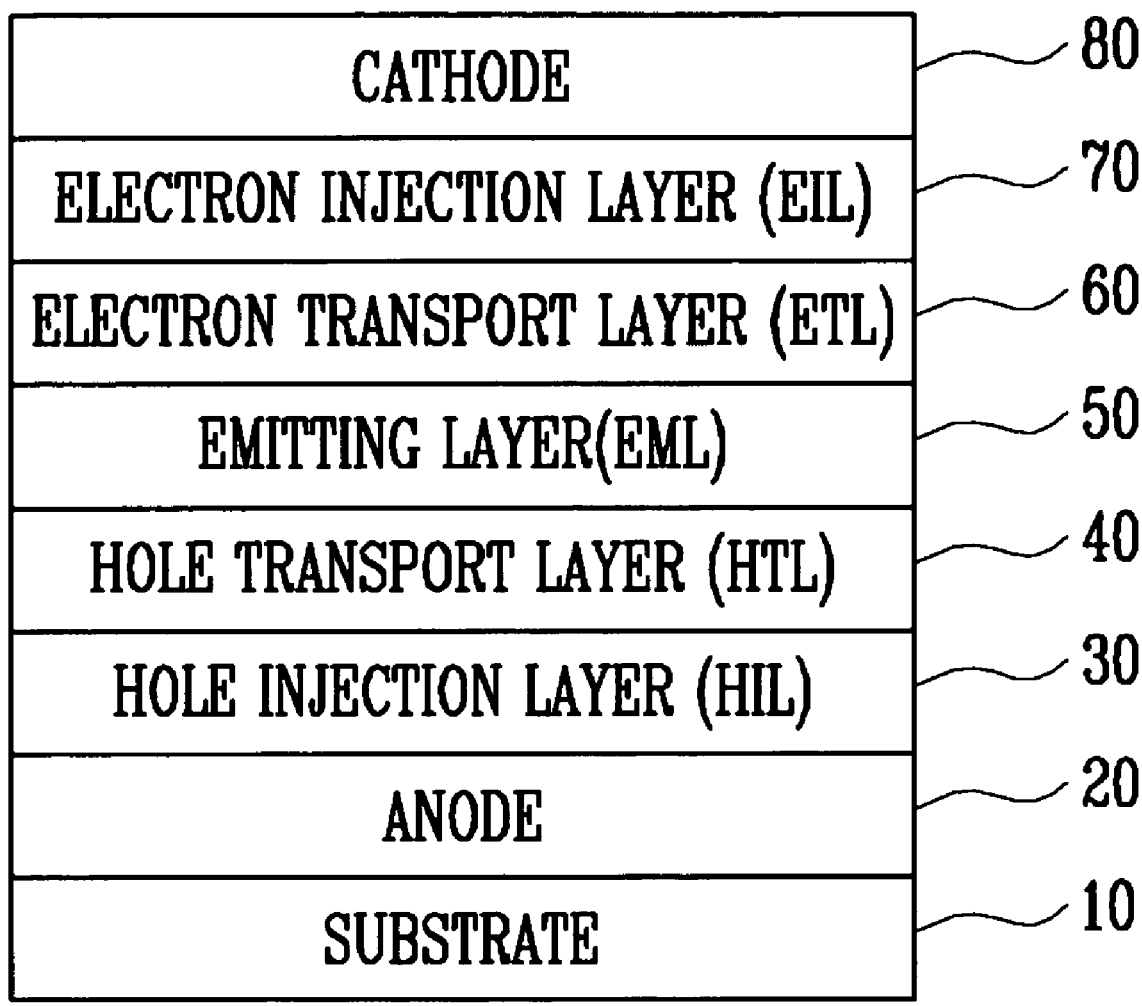
FIG. 7 shows the structure of the organic electroluminescence device of the present embodiments.

The organic electroluminescence device of the present embodiments can take the general form of a conventional photoluminescence device, or it can also be modified. Basically, the structure of organic electroluminescence device contains an organic layer (emitting layer) between the first electrode (anode) and the second electrode (cathode), and can additionally include a hole injection layer, a hole transport layer, a hole blocking layer, an electron injection layer, or an electron transport layer. FIG. 7 shows the details of the structure of the organic electroluminescence device of the present embodiments.

As shown in FIG. 7, the organic electroluminescence device of the present embodiments can take the structure having an emitting layer (50) between an anode (20) and a cathode (80), and in particular, can additionally include a hole injection layer (30) and a hole transport layer (40) between the anode (20) and the emitting layer (50) and an electron transport layer (60) and an electron injection layer (70) between the emitting layer (50) and the cathode (80).

The organic electroluminescence device shown in FIG. 7 is prepared by the following processes.

First, the top of the substrate (10) is coated with materials for an anode to form an anode (20). Herein, any generally accepted substrate can be used as the substrate of the embodiments, but particularly glass substrate or transparent plastic substrate is preferred owing to their excellent transparency and water-resistance, flatness of surface, and ease in handling. As an anode electrode material generated on the substrate, indium tin oxide (ITO), tin oxide (SnO$_2$), and zinc oxide (ZnO), having great transparency and conductivity can be used.

Next, a hole injection layer (HIL) (30) is selectively formed on the anode (20) by a conventional method such as vacuum deposition or spin coating. Materials for the hole injection layer are not limited but examples include CuPc (copper phthalocyanine) or IDE 406 (Idemitsu Kosan Co.).

Then, the hole transport layer (HTL) (40) is formed on the hole injection layer (30) by vacuum deposition or spin coating. Materials for the hole transport layer are not limited, but examples include N,N'-bis(3-methylphenyl)-N,N'-diphenyl-[1,1-biphenyl]-4,4'-diamine (TPD), and N,N'-di(naphthalene-1-yl)-N,N'-diphenylbenzidine (a-NPD).

Further, an emitting layer (EML) (50) is formed on the hole transport layer (40). As a material forming the emitting layer, the organic metal compound of the embodiments in which compounds for host and compounds for dopant are connected can be adopted singly or together with other host materials such as CBP (4,4'-bis(carbazole-9-yl)-biphenyl). In the organic metal compound of the present embodiments, the energy gap of compounds for host is identical to or different from that of compounds for dopant, and the energy gap should not be over about 400 nm. A preferred example of the organic metal compound of the embodiments is the compound represented by formula 1.

The organic metal compound can form the emitting layer and be deposited using using vacuum deposition as well as a wet process since the compound has the structure in which compounds for host are connected with compounds for dopant, increasing solubility with the increase of molecular weight. For example, spin coating, inkjet or laser thermal transfer method can be used but the method is not limited thereto.

When the organic metal compound of the present embodiments in which compounds for host and compounds for dopant are connected is accepted, the level of doping is regulated by the number of molecules for host to be linked to compounds for dopant. For example, when two molecules for host are connected to compounds for dopant, as shown in formula 6, the level of doping is about 33%, when 4 host molecules are connected to compounds for dopant, as shown in formula 10, the level of doping is about 20%, and when 8 host molecules are connected to compounds for dopant, as shown in formula 12, the level of doping is about 11%, indicating that the level of doping decreases with the increase of the number of host molecules.

The hole blocking layer (HBL) may be selectively formed on top of the emitting layer (50) to prevent an exiton from migrating to the electron transport layer(60) or holes from migrating to electron transport layer (60). The hole blocking layer forming materials are not limited, but examples include phenanthroline compounds (for example, BCP). The hole blocking layer can be formed by vacuum deposition or spin coating.

The electron transport layer (ETL) (60) can be formed on the emitting layer (50), using, for example, vacuum deposition or spin coating. The electron transport layer forming materials are not limited, but examples include aluminum complexes, for example Alq3 (tris(8-quinolinolato)-aluminum).

The electron injection layer (EIL) (70) can be formed on the electron transport layer (60) by vacuum deposition or spin coating. The electron injection layer forming materials are not limited but examples include LiF, NaCl, CsF, etc.

The cathode (80) can be also formed on the electron injection layer (70) by vacuum deposition, which is the final step for the generation of a photoluminescence device. Materials used for the formation of the cathode are exemplified by Li, Mg, Al, Al—Li, Ca, Mg—In, and Mg—Ag.

Although the organic electroluminescence device of the present embodiments has a laminate structure shown in FIG. 7, the device can additionally include one or two intermediate layers, such as hole blocking layers, etc. The thickness of each layer of the photoluminescence device can be determined depending on the specific function of the device and includes, for example, the generally acceptable range for such devices.

The present embodiments are described more precisely hereinafter, but the present embodiments are not limited to these specific examples.

Reagents

Products of Across Co.: 2-bromo-4-methylpyridine; potassium phosphate tribasic monohydrate; 1,4-dioxane; copper iodide; (+,−)-trans-1,2-diamino-cyclohexane; and 3,5-dihydroxybenzyl alcohol Products of Aldrich Co.: tetrakis-(triphenylphosphine)palladium; 2,4-difluorophenylboronic acid; NBS (N-bromosuccinimide); AIBN (azobisisobutyronitrile); 1,3-dibromo-5-methylbenzene, 18-crown-6; acetone; phosphorous tribromide; and cesium carbonate Products of Duksan Chemical Co.: methylene chloride; magnesium sulfate; carbon tetrachloride; hexane; and diethyl ether Others: potassium carbonate (Daejung), dimethoxyethane (TCI), hydroquinone (MAY & BAKER), carbazole and acetonitrile (Fisher)

Confirmation of Compounds

The structures of all the compounds newly synthesized were examined with $^1$H-NMR and $^{13}$C-NMR and UV and spectrofluorometer. Results of $^1$H-NMR and $^{13}$C-NMR were recorded by a Bruker AM-300 spectrometer. A BECKMAN DU-650 recorded the results for UV and JASCO FP-7500 recorded the results for the spectrofluorometer. All the chemical mobilities were recorded by the unit of ppm according to a solvent.

EXAMPLE 1

In the present embodiments, the compound of formula 6 is synthesized based on formula 1, in which X is X1, M is Ir, R$_1$-R$_8$ are H, a is 1, m-n are 2, and L is picolinate. The synthetic reaction formula is as follows.

Reaction Scheme 1

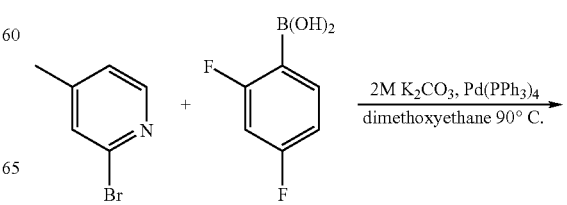

-continued
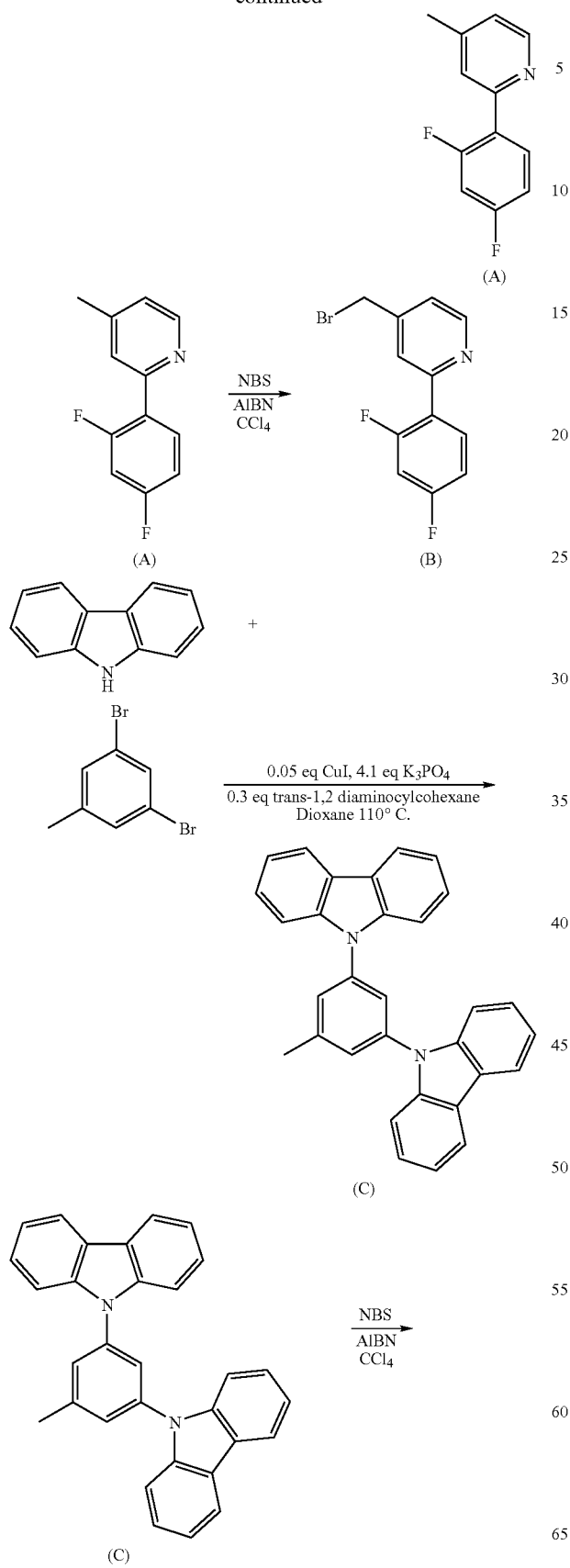
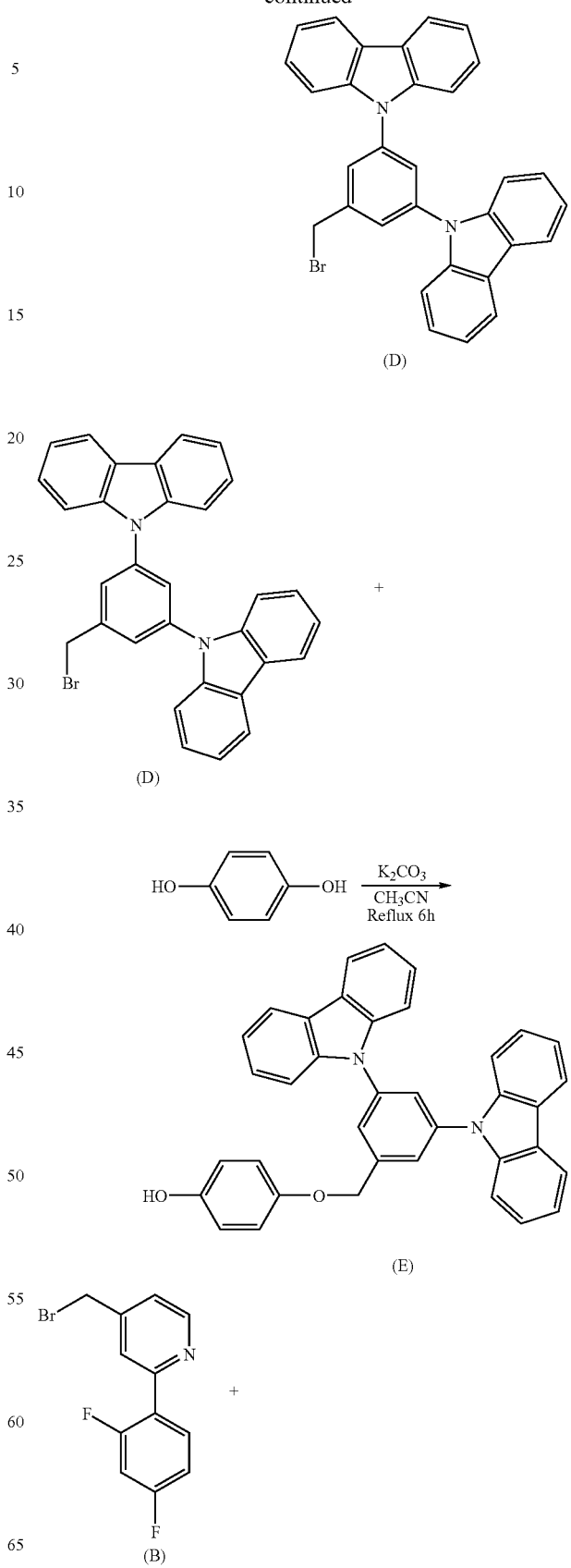

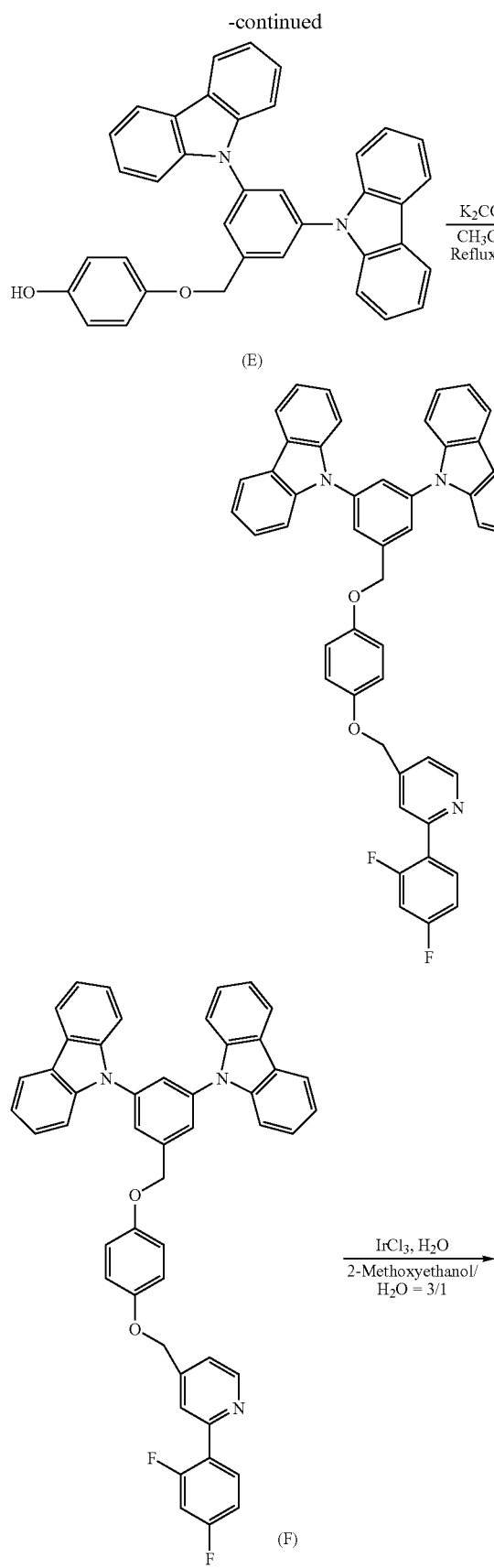
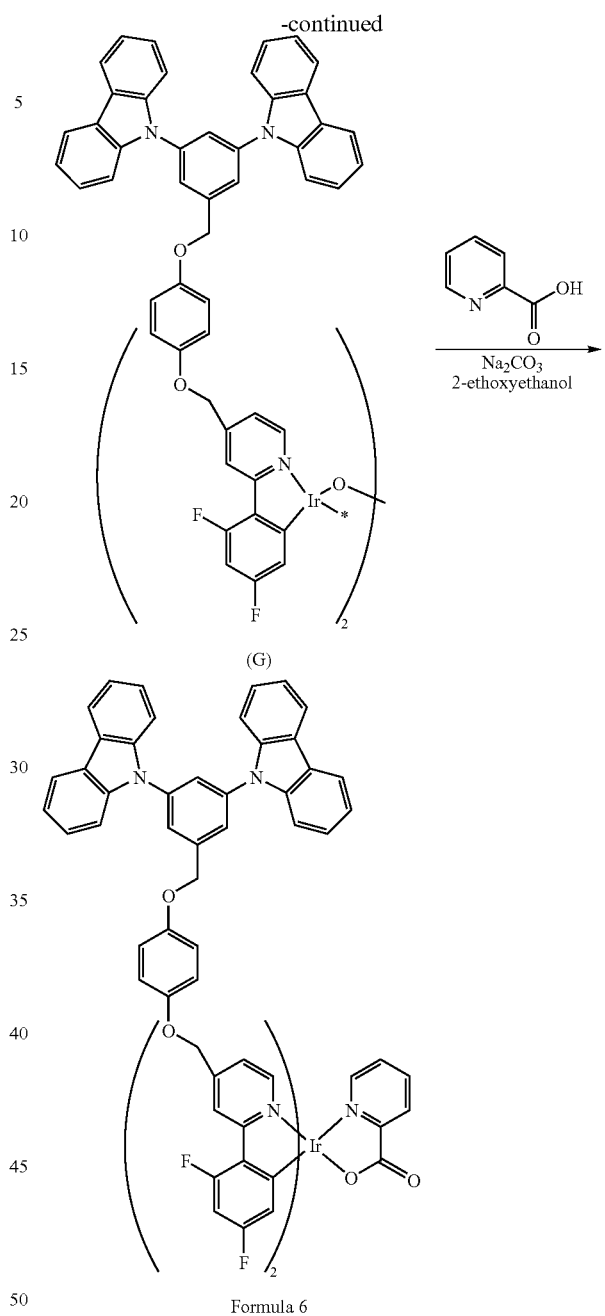

Synthesis of (A)

2-bromo-4-methylpyridine (1 mmol), 2,4-difluorophenylboronic acid (1.2 mmol), potassium carbonate (2.7 mmol), and dimethoxyethane (1.5 mL) were put together in a round bottom flask, to which nitrogen was injected, followed by stirring for 30 minutes. Tetrakis(triphenylphosphine)palladium (0.05 mmol) was added and a reflux condenser was connected thereto, followed by reflux at 90° C. for 18 hours. After confirming the reaction by TLC, the solvent was removed by distillation under reduced pressure at high vacuum. After extracting with ethyl acetate, the residue was purified by a fresh column to give compound (A). The yield was 93%.

$^1$H-NMR(300 MHz, CDCl$_3$): d(ppm) 8.59 (d, J=3.0 Hz, 1H), 7.99 (dd, J=6, 1.5 Hz, 1H), 7.60 (s, 1H), 7.13 (d, J=3 Hz, 1H), 7.03 (d, J=3.9 Hz, 1H), 6.97-6.90 (m, 2H), 2.45 (s, 3H)

Synthesis of (B)

The compound (A) (1 mmol), NBS (1.3 mmol) and AIBN were put together in CCl$_4$ solvent, followed by heat-stirring at 80° C. for 24 hours. The reaction was confirmed by TLC, followed by filtering. The filtrate was washed with water and NaCl, and the solvent was removed under high vacuum. The residue was recrystallized from hexane and diethyl ether to give compound (B) as a brown solid. The yield was 30%.

$^1$H-NMR(300 MHz, CDCl$_3$): d(ppm) 8.70 (d, J=2.5 Hz, 1H), 8.03(q, J=6, 1.8 Hz, 1H), 7.78 (s, 1H), 7.30 (d, J=2.3 Hz, 1H), 7.03-6.92 (m, 2H), 4.47 (s, 2H)

Synthesis of (C)

Copper iodide (0.01 mmol), potassium phosphate tribasic monohydrate (2.1 mmol), carbazole (1.2 mmol), and 1,4-dioxane (10 mL) were put in an airtight tube, to which nitrogen was injected, followed by stirring for 30 minutes. 1,3-dibromo-5-methylbenzene, and (+,−)-trans-1,2-diaminocyclohexane (0.1 mmol) were added into the tube, which was then tightly sealed, followed by heat-stirring at 110° C. for 24 hours.

The reaction was confirmed by TLC. The solvent was filtered by a glass filter and then removed by distillation under reduced pressure. Fresh column purification with methylene chloride was performed, resulting in a solid material. The product was dried for 3 hours by vacuum pump to give compound (C). The yield was 60%. $^1$H-NMR (300 MHz, ((CD$_3$)$_2$CO)): d (ppm) 8.24 (d, J=3.8 Hz, 4H), 7.71 (s, 1H), 7.70-7.64 (m, 6H), 7.48 (t, J=7.7 Hz, 4H), 7.31 (t, J=8.5 Hz, 4H) 2.68 (s, 3H)

Synthesis of (D)

The compound (C) (0.1 mmol), NBS (0.1 mmol) and AIBN were put together in CCl$_4$ solvent, followed by heat-stirring at 80° C. for 12 hours. The reaction was confirmed by TLC, followed by filtering. The filtrate was washed with water and NaCl, and the solvent was removed under high vacuum. The residue was recrystallized from hexane and diethyl ether to give compound (D) as a brown solid. The yield was 40%.

$^1$H-NMR(CDCl3, 300 MHz): d(ppm) 8.18 (d, J=3.8 Hz, 4H), 7.80 (s, 1H), 7.76 (s, 2H), 7.58(d, J=4.2 Hz, 4H), 7.48 (t, J=8.2 Hz, 4H), 7.35 (t, J=7.7 Hz, 4H), 4.69 (s, 2H)

Synthesis of (E)

The compound (D) (1 mmol), hydroquinone (1 mmol), K$_2$CO$_3$ (1 mmol) and CH$_3$CN (20 mL) were put together in a round bottom flask, followed by reflux at 80° C. for 6 hours. The reaction was confirmed by TLC, followed by filtering and washing with CH$_2$Cl$_2$. The filtrate was washed with water and NaCl and the solvent was removed under high vacuum. The residue was purified with a fresh column to give compound (E). The yield was 72%.

$^1$H-NMR(CDCl$_3$, 300 MHz): d(ppm) 8.17 (d, J=3.8 Hz, 4H), 7.78-7.77 (br s, 3H), 7.53(d, J=4.1 Hz, 4H), 7.45 (t, J=8.7 Hz, 4H), 7.33 (t, J=7.8 Hz, 4H), 6.94 (d, J=4.5 Hz, 2H), 6.84 (d, J=4.5 Hz, 2H), 5.28 (s, 2H)

Synthesis of (F)

The compound (E) (0.06 mmol), the compound (B) (0.065 mmol), K$_2$CO$_3$ (0.012 mmol) and CH$_3$CN (20 mL) were put together in a round bottom flask, followed by reflux at 80° C. for 10 hours. After confirming the reaction by TLC, impurities were eliminated by filtering. The filtrate was washed with CH$_2$Cl$_2$, water and NaCl. The solvent was removed under high vacuum. The residue was purified with a fresh column to give compound (F). The yield was 65%.

Synthesis of the Compound of Formula 6

Iridium chloride hydrochloride hydrate (0.04 mmol) and the compound (F) (0.08 mmol) were added thereto, followed by stirring at 130° C. for 10 hours under a nitrogen atmospher. After confirming the reaction by TLC, H$_2$O was added to obtain a solid material. The product was filtered and then dried for 3 hours by vacuum pump to give compound (G). The yield was 50%.

2-ethoxyethanol (15 ml) was purged with N$_2$ for 30 minutes with stirring. The compound (G) (0.05 mmol) and picolinic acid (0.15 mmol) were added thereto, together with Na$_2$CO$_3$ (0.5 mmol) as a base. The reaction mixture was heat-stirred at 130° C. for 5 hours in the presence of nitrogen, and the reaction was confirmed by TLC. The solvent was eliminated by distillation under reduced pressure at high vacuum, followed by extraction with methylene chloride. The extracted methylene chloride layer was washed with saturated NaCl solution, and then dried over MgSO$_4$. After removing the solvent by distillation under reduced pressure at high vacuum, the residue was added with hexane, resulting in a solid material. After filtering, the filtrate was purified by column chromatography, which was then dried for 3 hours by vacuum pump to give the compound of formula 6. The yield was 60%.

$^1$H-NMR (300 MHz, ((CD$_3$)$_2$CO)): d (ppm) 8.70 (d, J=3 Hz, 1H), 8.41 ( s, 1H), 8.22 (d, J=3.9 Hz 8H), 8.17 (s, 1H), 8.11 (t, J=3.8 Hz, 1H), 7.89-7.86 (m, 6H), 7.72 (d, J=3 Hz, 1H), 7.60-7.53 (m, 10H), 7.45 (t, J=7.7 Hz, 8H), 7.30 (t, J=7.5 Hz, 8H), 7.08 (s, 8H), 6.59-6.47 (m, 2H), 5.92 (d, J=6 Hz, 1H), 5.56 (d, J=6 Hz, 1H) 5.46 (s, 4H), 5.41 (s, 4H)

EXAMPLE 2

In the present embodiments, the compound of formula 8 is synthesized based on formula 1, in which X is X1, M is Ir, R$_1$-R$_8$ are H, a is 1, m-n are 2, and L is 1,5-dimethyl-3-pyrazole-carboxylate. The synthetic reaction scheme is as follows.

Reaction Scheme 2

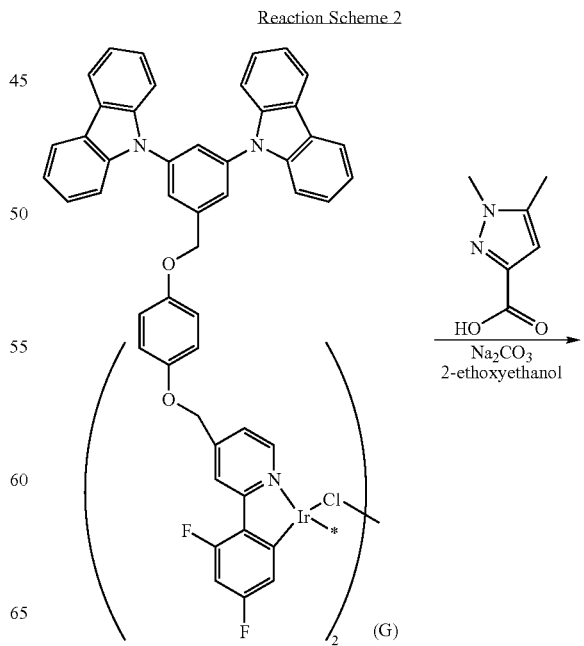

-continued

[Formula 8]

Synthesis of the Compound of Formula 8

2-ethoxyethanol (15 ml) was purged with $N_2$ for 30 minutes with stirring. The compound (G) (0.05 mmol), 3,5-dimethylpyrazolecarboxylic acid (dm3pc 0.15 mmol) and $Na_2CO_3$ (0.5 mmol) as a base were added thereto. The reaction mixture was heat-stirred at 130° C. for 5 hours in the presence of nitrogen, and the reaction was confirmed by TLC. The solvent was eliminated by distillation under reduced pressure, followed by extraction with methylene chloride. The extracted methylene chloride layer was washed with saturated NaCl solution, and then dried over $MgSO_4$. After removing the solvent by distillation under reduced pressure at high vacuum, the residue was added to hexane, resulting in a solid material. After filtering, the filtrate was purified by column chromatography, which was then dried for 3 hours by vacuum pump to give the compound of formula 8. The yield was 60%.

$^1$H-NMR (300 MHz, $((CD_3)_2CO)$): d(ppm) 8.75 (d, J=3.0 Hz, 1H), 8.44 (d, J=3.2 Hz, 1H), 8.39 (s, 1H), 8.27 (d, J=4.1 Hz, 8H), 7.93-7.89 (br s, 8H), 7.62-7.57 (m, 10H), 7.47 (t, J=6.8 Hz, 8H), 7.32 (t, J=9.7 Hz, 8H), 7.12 (d, J=4.8 Hz, 8H), 6.60-6.48 (m, 2H), 6.44 (s, 1H), 5.92 (d, J=6 Hz, 1H), 5.48 (br s 4H) 5.45 (br s, 4H), 3.21 (s, 3H), 2.26 (s, 3H).

EXAMPLE 3

In the present embodiments, the compound of formula 10 is synthesized based on formula 1, in which X is X2, M is Ir, $R_1$-$R_7$ and $R_9$-$R_{10}$ are H, a is 2, b is 1, m-n are 2, and L is picolinate. The synthetic reaction scheme is as follows.

Reaction Scheme 3

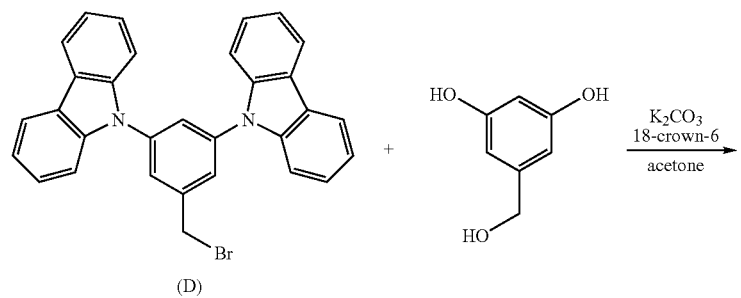

(D)

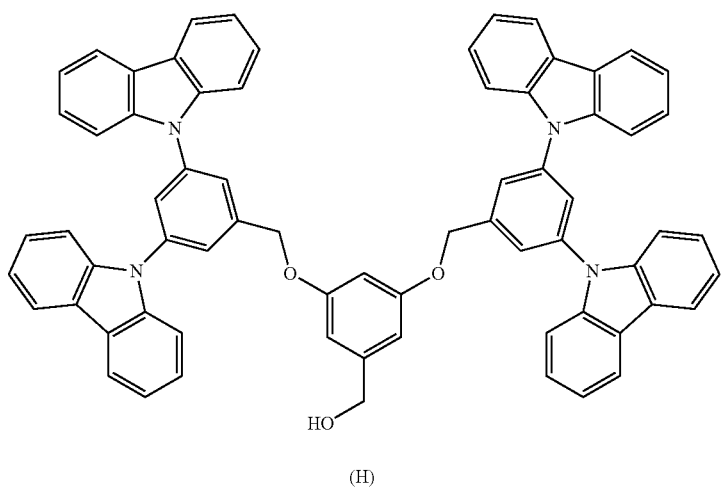

(H)

-continued
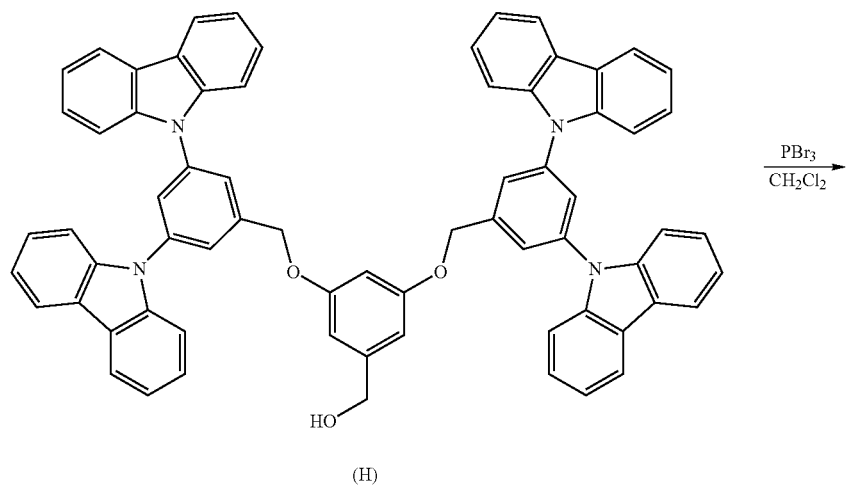
(H)
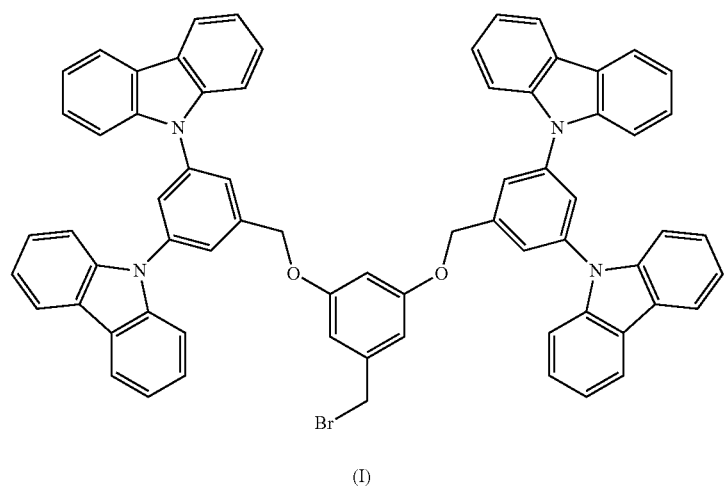
(I)
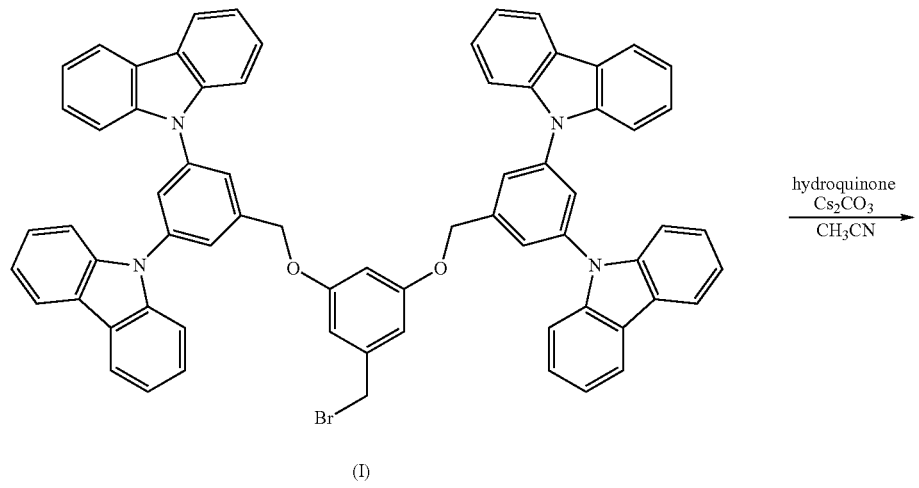
(I)

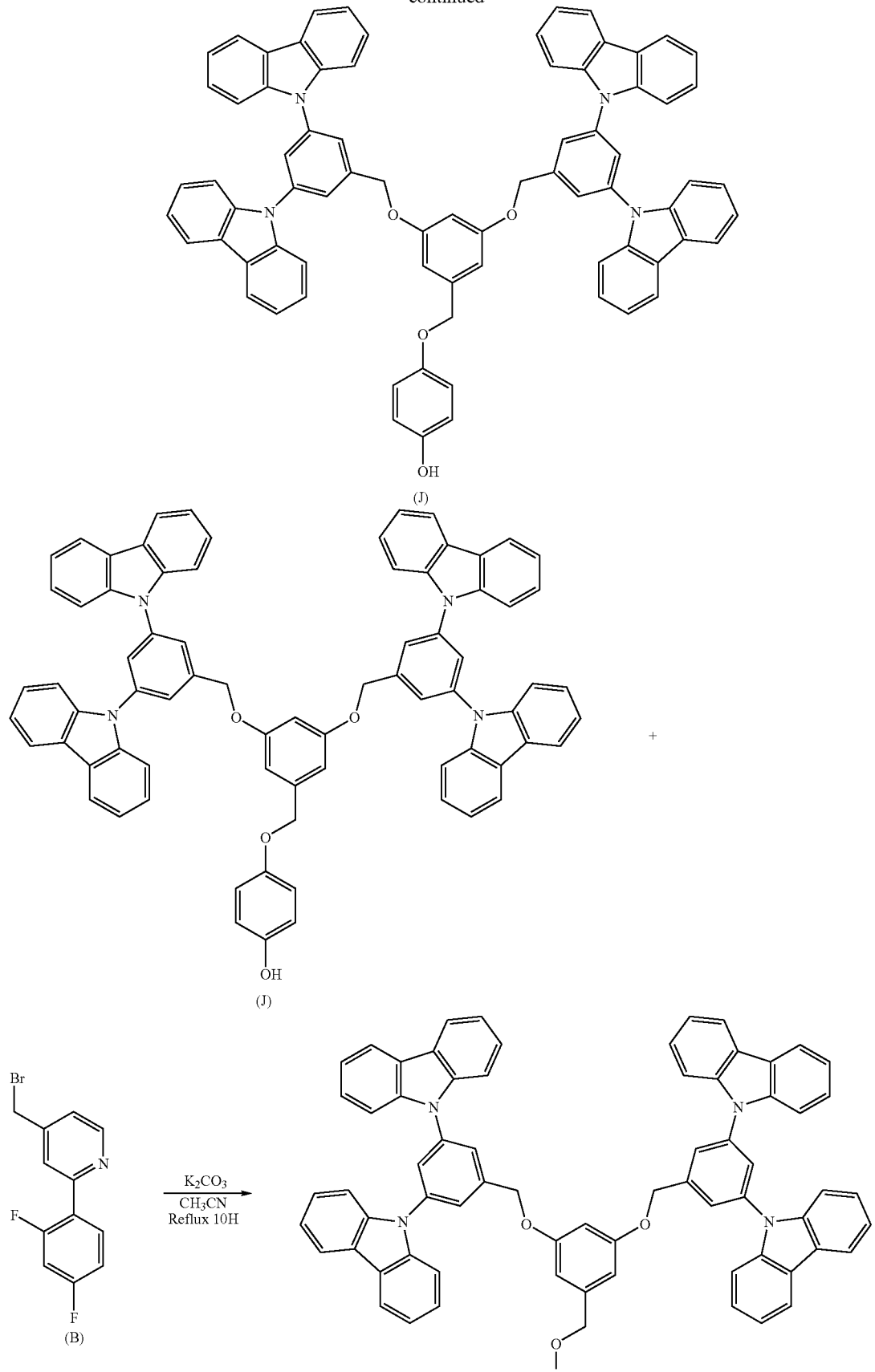

-continued
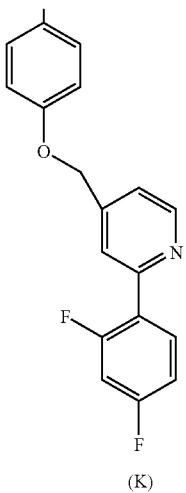
(K)
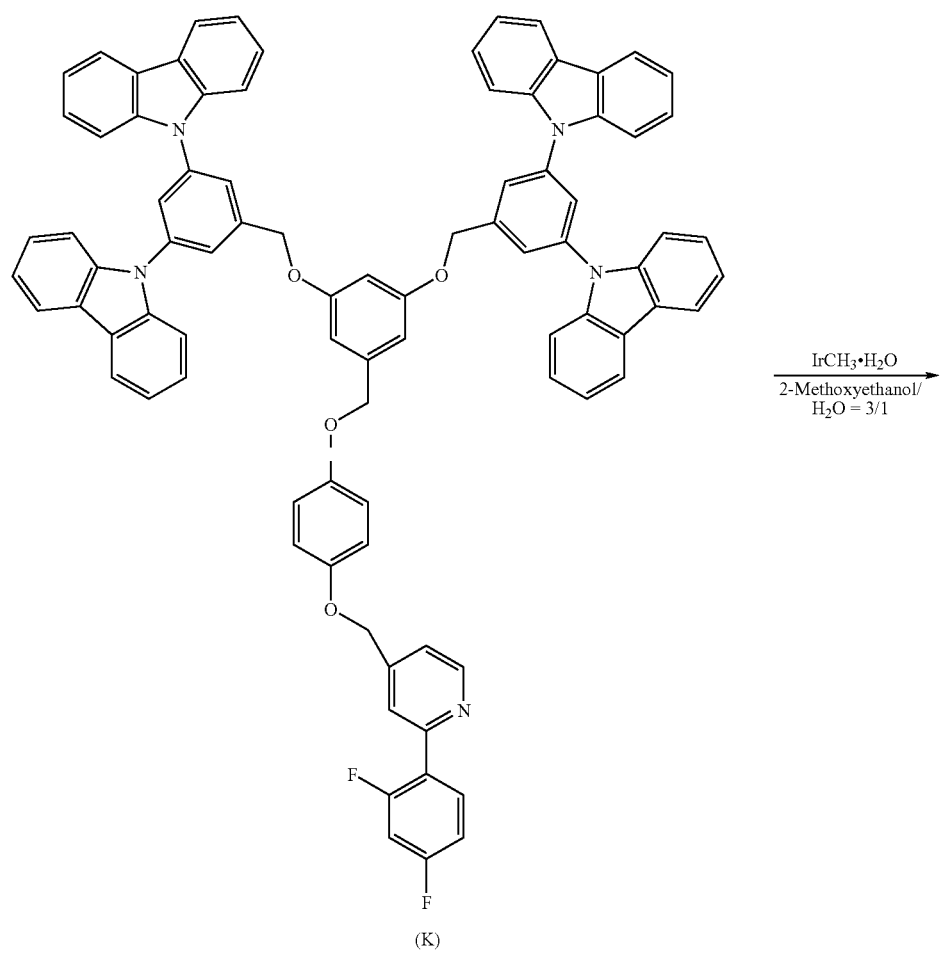
(K)

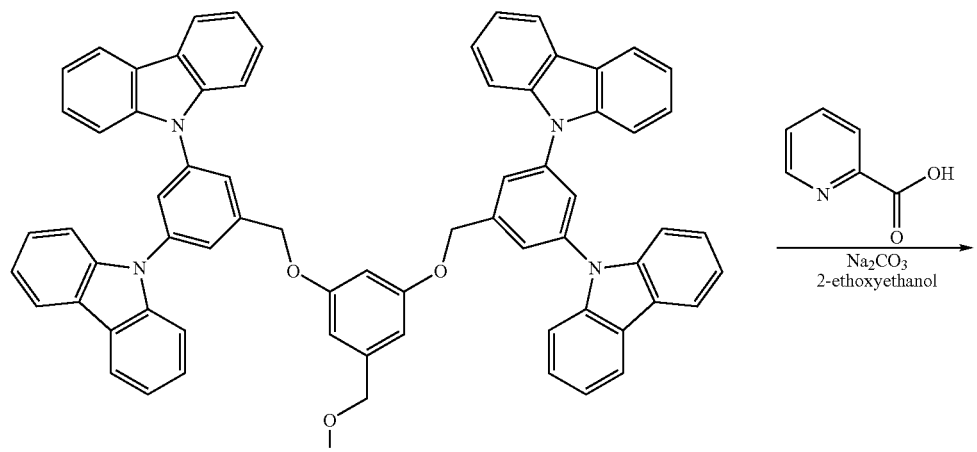
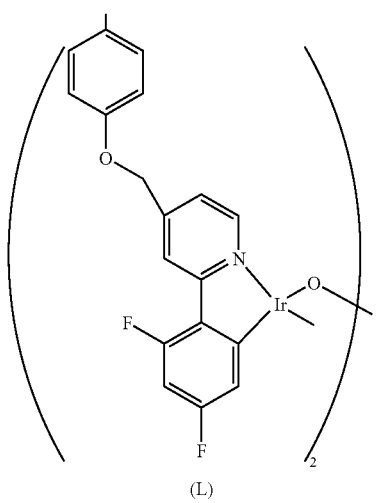
(L)
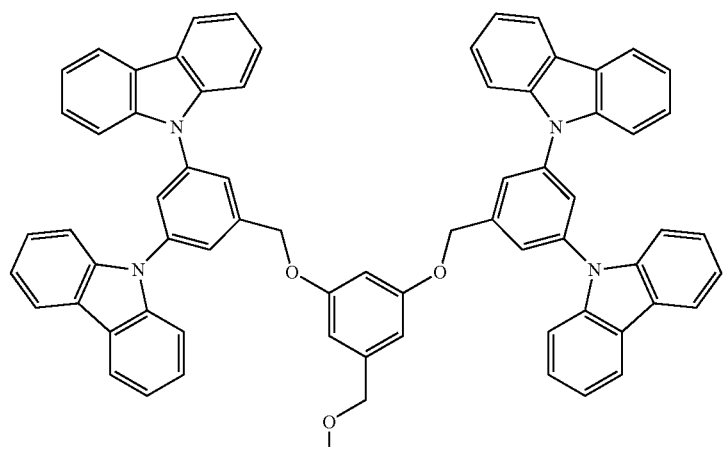

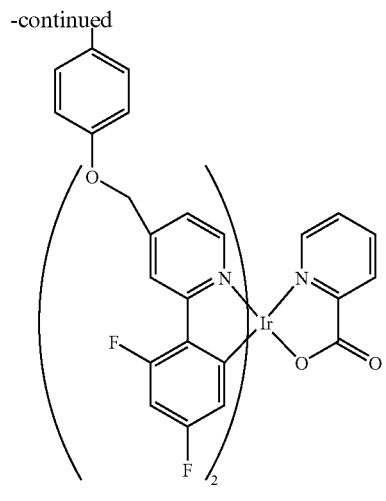

Formula 10

Synthesis of (H)

The compound (D) (1 mmol), 3,5-dihydroxybenzyl alcohol (0.5 mmol), $K_2CO_3$ (1.25 mmol), 18-crown-6 (0.1 mmol), and acetone (20 ml) were put together in a round bottom flask, followed by reflux at 50° C. for 10 hours. After confirming the reaction by TLC, the reaction mixture was filtered and washed with $CH_2Cl_2$. The filtrate was washed with water and NaCl. The solvent was removed under high vacuum. The residue was purified with a fresh column to give compound (H). The yield was 76%.

$^1$H-NMR(($CD_3$)$_2$CO), 300 MHz: d(ppm) 9.19 (d, J=7.8 Hz, 8H), 7.89(s, 4H), 7.88(s, 2H), 7.57(d, J=8.4, H=8), 7.40 (q, J=6.9, H=8), 7.26(t, J=7.8, H=8), 6.85(s, H=2), 6.82(s, H=1), 5.53(s, H=4), 4.66(d, J=5.7, H=2).

Synthesis of (I)

The compound (H) (1 mmol) was put in a round bottom flask, to which $CH_2Cl_2$ (40 mL) was added. The temperature was lowered to 0° C. Phosphorous tribromide (1.2 mmol) was added thereto, followed by stirring for 3 hours. After confirming the reaction by TLC, the reaction mixture was washed with water and NaCl using a separatory funnel. After eliminating the organic solvent, purification with a fresh column was performed to give solid compound (I). The yield was 90%.

$^1$H-NMR($CDCl_3$, 300 MHz): d(ppm) 8.14 (d, J=3.9 Hz, 8H), 7.77 (s, 3H), 7.52 (d, J=4.1 Hz, 4H), 7.43 (t, J=8.1 Hz, 4H), 7.32 (t, J=3.5 Hz, 4H), 6.76 (s, 2H), 6.69 (s, 1H), 5.32 (s, 4H), 4.46 (s, 2H)

Synthesis of (J)

The compound (I) (1 mmol), hydroquinone (2 mmol), cesium carbonate (2 mmol), and acetonitrile (50 mL) were put together in a round bottom flask. The reaction mixture was heat-stirred at 80° C. for 10 hours. After confirming the reaction by TLC, the reaction mixture was filtered. The filtrate was washed with water and NaCl. The solvent was removed under high vacuum. The residue was purified with a fresh column to give solid compound (J). The yield was 62%.

$^1$H-NMR($CDCl_3$, 300 MHz): d(ppm) 8.15 (d, J=3.8 Hz, 8H), 7.77 (s, 3H), 7.51 (d, J=4.1 Hz, 4H), 7.42 (t, J=7.5 Hz, 4H), 7.32 (t, J=3.9 Hz, 4H), 6.82 (d, J=1.2 Hz, 2H) 6.80 (br s, 2H), 6.67 (d, J=2.4 Hz, 2H), 6.65 (br s, 1H), 5.32 (s, 4H), 5.00 (s, 2H)

Synthesis of (K)

The compound (J) (1 mmol), the compound (B) (0.3 mmol), $K_2CO_3$ (0.15 mmol), and $CH_3CN$ (20 mL) were put together in a round bottom flask, followed by reflux at 80° C. for 10 hours. After confirming the reaction by TLC, impurities were eliminated by filtering. After washing with $CH_2Cl_2$, the filtrate was washed with water and NaCL. The solvent was removed under high vacuum. The residue was purified with a fresh column to give solid compound (K). The yield was 77%.

$^1$H-NMR (300 MHz, (($CD_3$)$_2$CO)): d (ppm) 8.64 (d, J=2.4 Hz, 1H), 8.19 (d, J=3.8 Hz, 8H), 8.15-8.10 (m, 1H), 7.88 (br s, 4H), 7.82 (br s, 2H), 7.79 (br s, 1H), 7.55 (d, J=4.1 Hz, 8H), 7.40 (t, J=8.3 Hz, 8H), 7.32 (d, J=2.4 Hz, 1H), 7.26 (t, J=7.9 Hz 8H), 7.19-7.13 (m, 2H), 6.95-6.79 (m, 7H), 5.56(s, 4H), 5.08 (s, 2H), 5.00 (s, 2H)

Synthesis of the Compound of Formula 10

Nitrogen was injected into 2-methoxyethanol (15 ml) at room temperature, followed by stirring for 30 minutes. Iridium chloride hydrochloride hydrate (0.04 mmol) and the compound (K) (0.08 mmol) were added thereto, followed by heat-stirring at 130° C. for 10 hours in the presence of nitrogen. After confirming the reaction by TLC, $H_2O$ was added to obtain a solid material. The product was filtered and then dried for 3 hours by vacuum pump to give compound (L). The yield was 50%.

Then, nitrogen was injected into 2-ethoxyethanol (15 ml) at room temperature, followed by stirring for 30 minutes. The compound (L) (0.05 mmol) and picolinic acid (0.15 mmol) were added thereto, together with $Na_2CO_3$ (0.5 mmol) as a base. The reaction mixture was heat-stirred at 130° C. for 5 hours in the presence of nitrogen, and the reaction was confirmed by TLC. The solvent was eliminated by distillation under reduced pressure at high vacuum, followed by extraction with methylene chloride. The extracted methylene chloride layer was washed with saturated NaCl solution, and then dried over $MgSO_4$. After removing the solvent by distillation under reduced pressure, the residue was added to hexane, resulting in a solid material. After filtering, the filtrate was purified by column chromatography, which was then dried for 3 hours by vacuum pump to give the compound of formula 10. The yield was 60%.

$^1$H-NMR (300 MHz, (CDCl$_3$)): d (ppm) 8.70 (d, J=2.9 Hz, 1H), 8.33 (d, J=3.9 Hz, 1H), 8.15 (s, 2H), 8.14 (d, J=3.82 Hz, 16H), 8.11 (t, J=7.8 Hz, 1H), 7.91 (t, J=3 Hz, 1H), 7.76-7.71 (br s, 12H), 7.51 (d, J=3.9 Hz, 16H), 7.41 (t, J=7.2 Hz, 16H), 7.31-7.26 (m, 17H), 7.18 (d, J=3.0 Hz, 1H), 7.01 (d, J=3.0 Hz, 1H), 6.88-6.85 (br d, 8H), 6.71 (br s, 2H), 6.48-6.39 (m, 2H), 5.84 (d, J=6 Hz, 1H), 5.59 (d, J=6 Hz, 1H) 5.33 (s, 8H), 5.03 (br s, 8H)

EXAMPLE 4

In the present embodiments, the compound of formula 12 is synthesized based on formula 1, in which X is X3, M is Ir, $R_1$-$R_7$ and $R_{11}$-$R_{13}$ are H, a is 2, b is 2, c is 1, (m-n) is 2, and L is picolinate. The synthetic reaction scheme is as follows.

Reaction Scheme 4

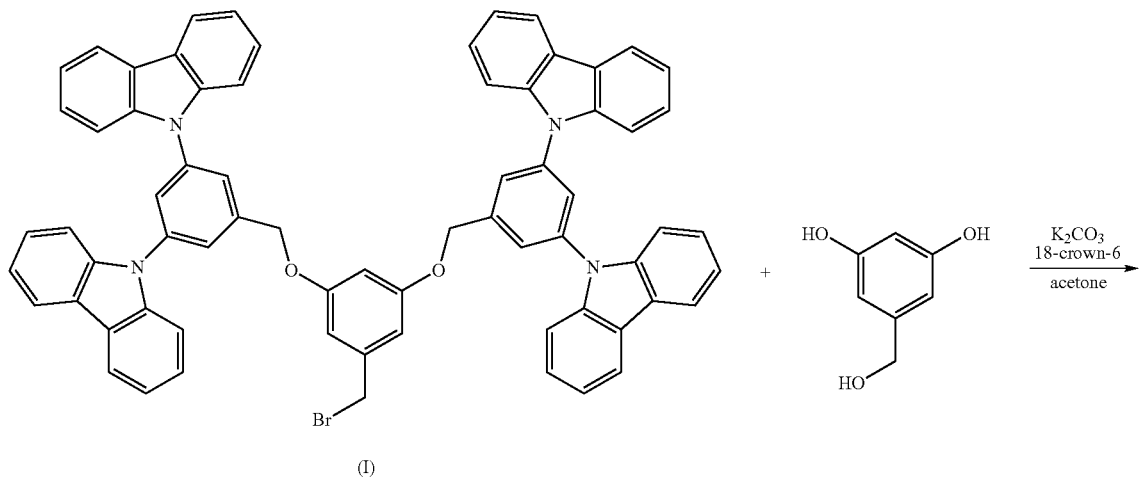

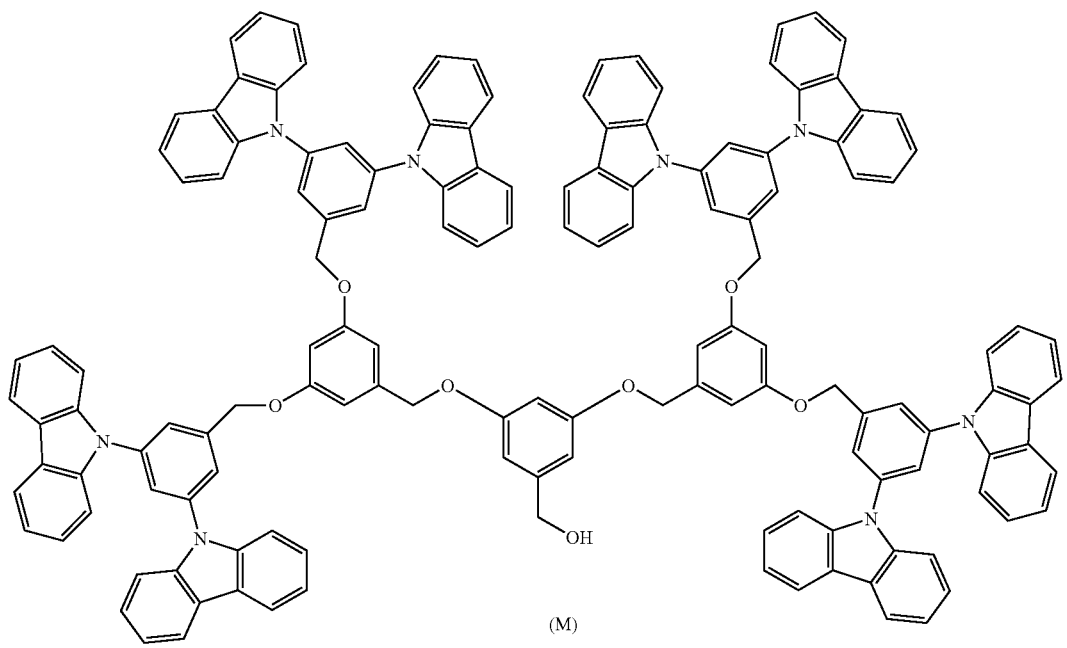

-continued
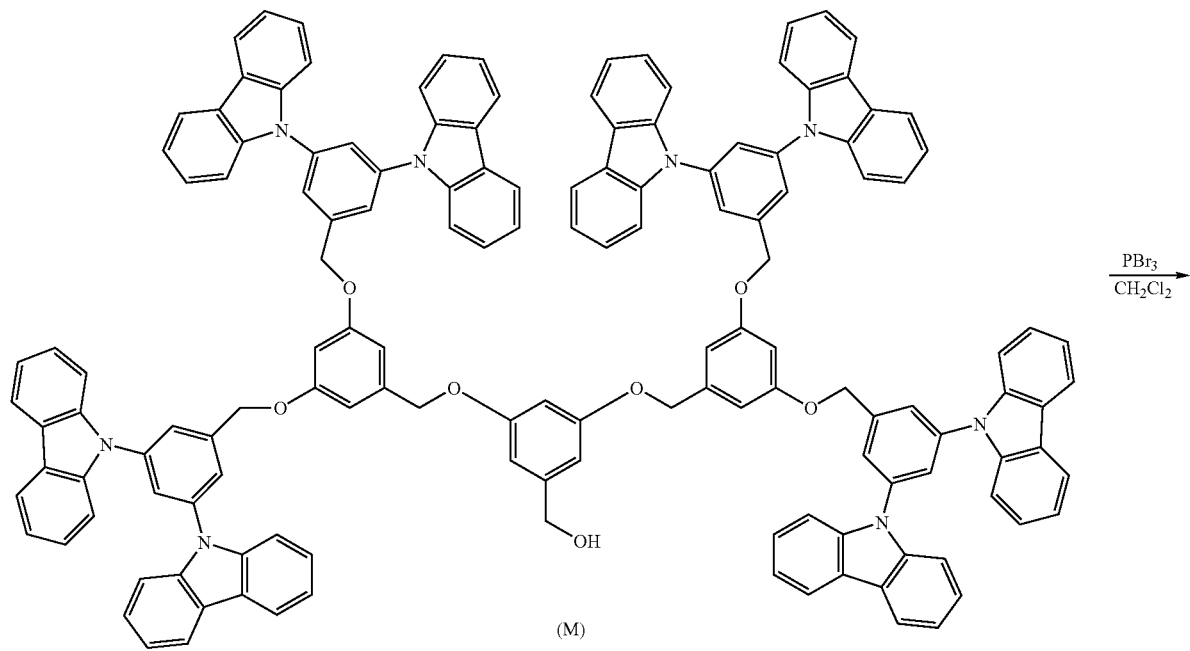
(M)
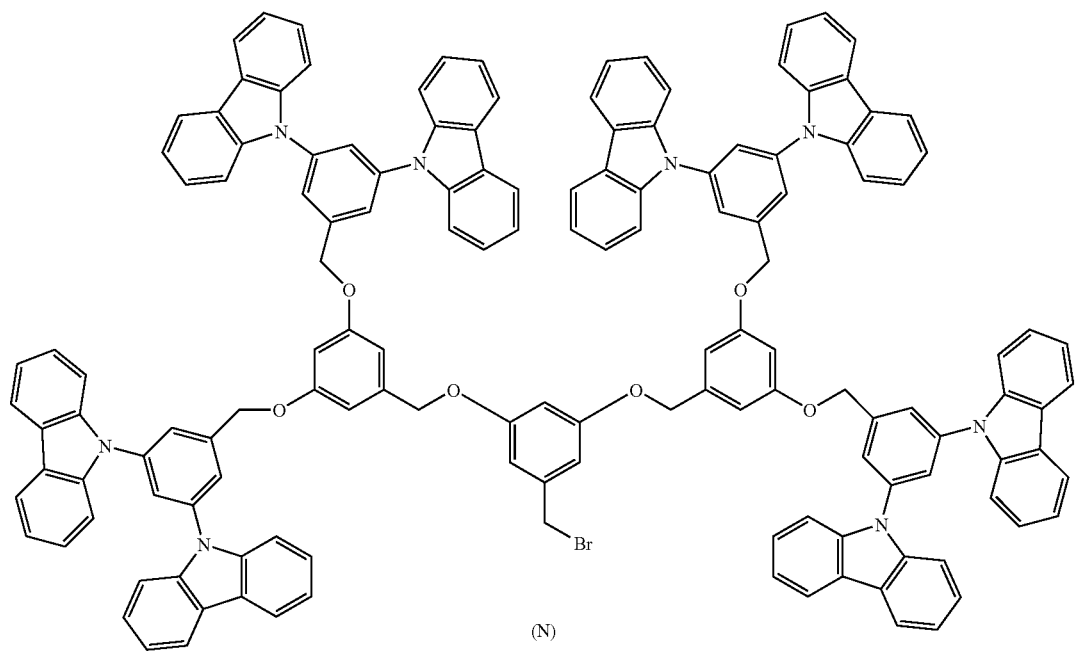
(N)

-continued
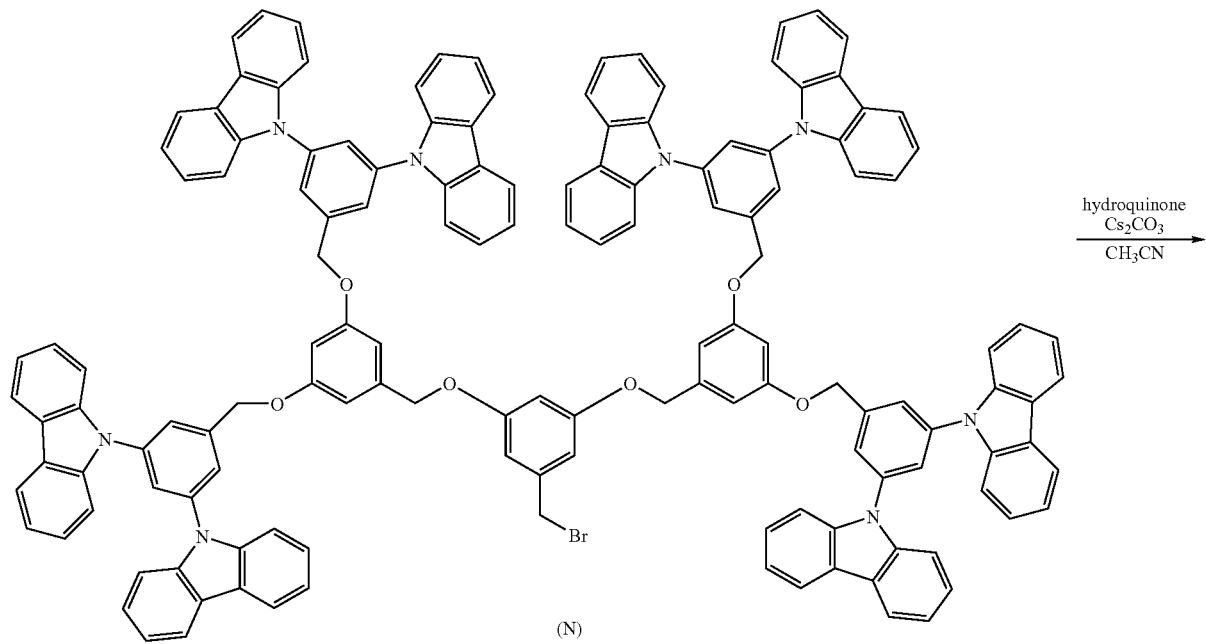
(N)
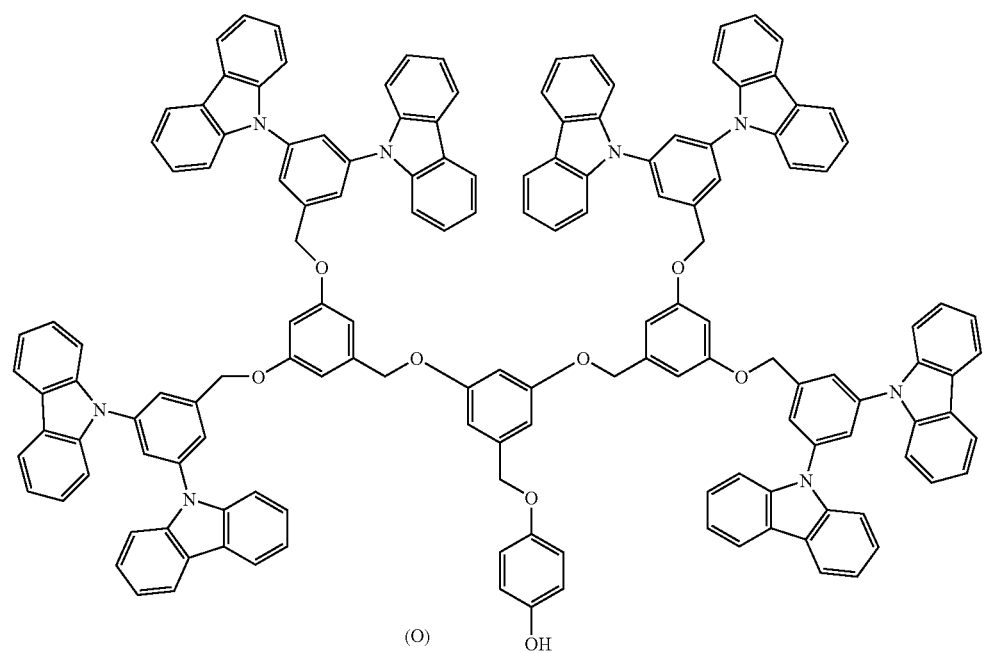
(O)

-continued
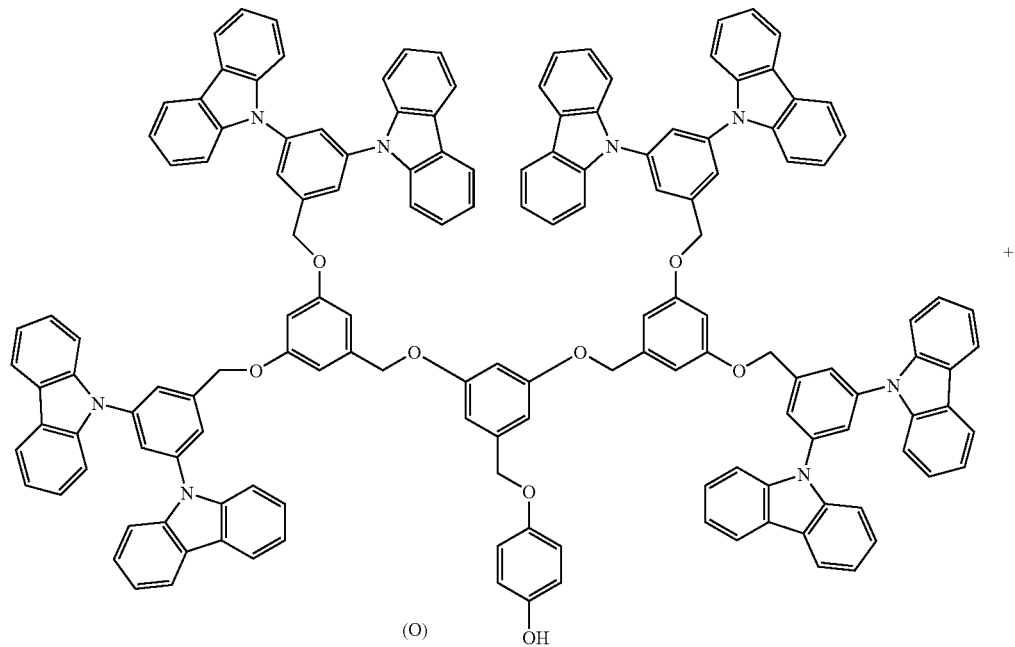
(O)
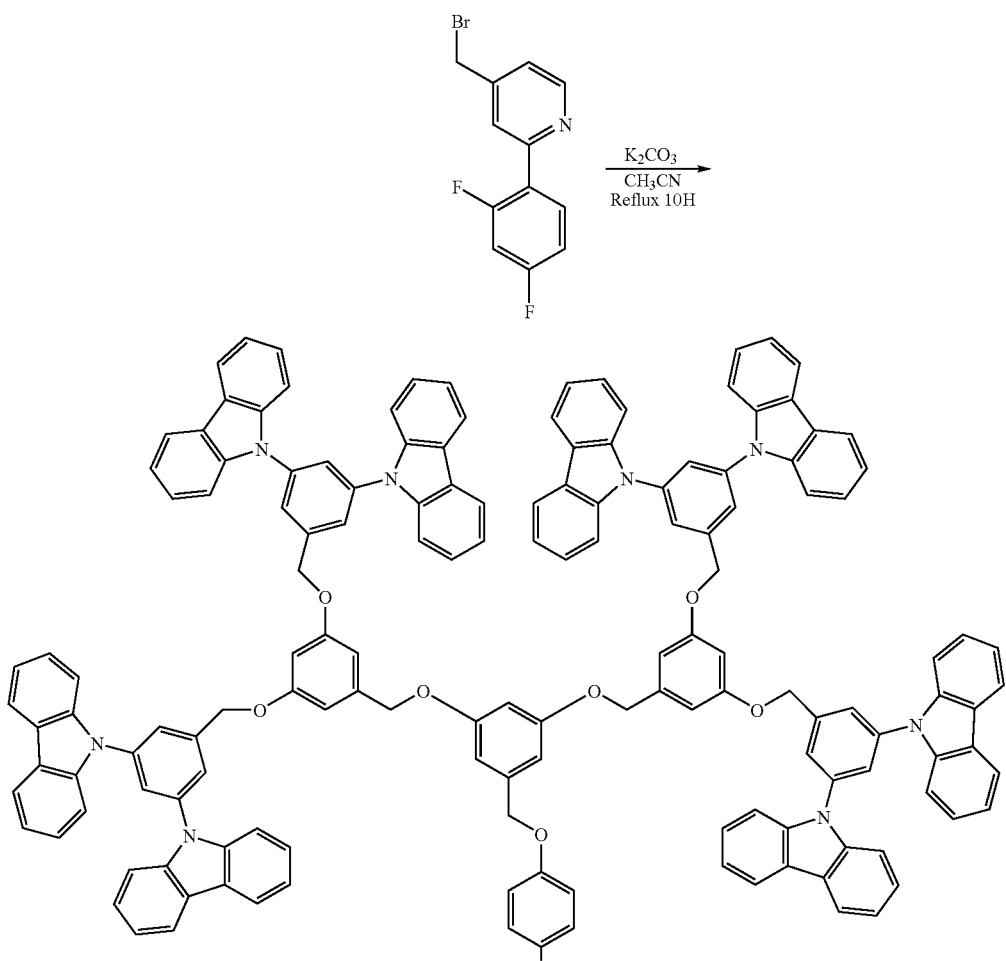

-continued
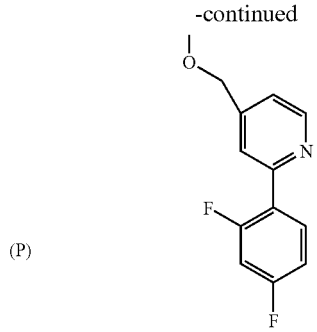
(P)
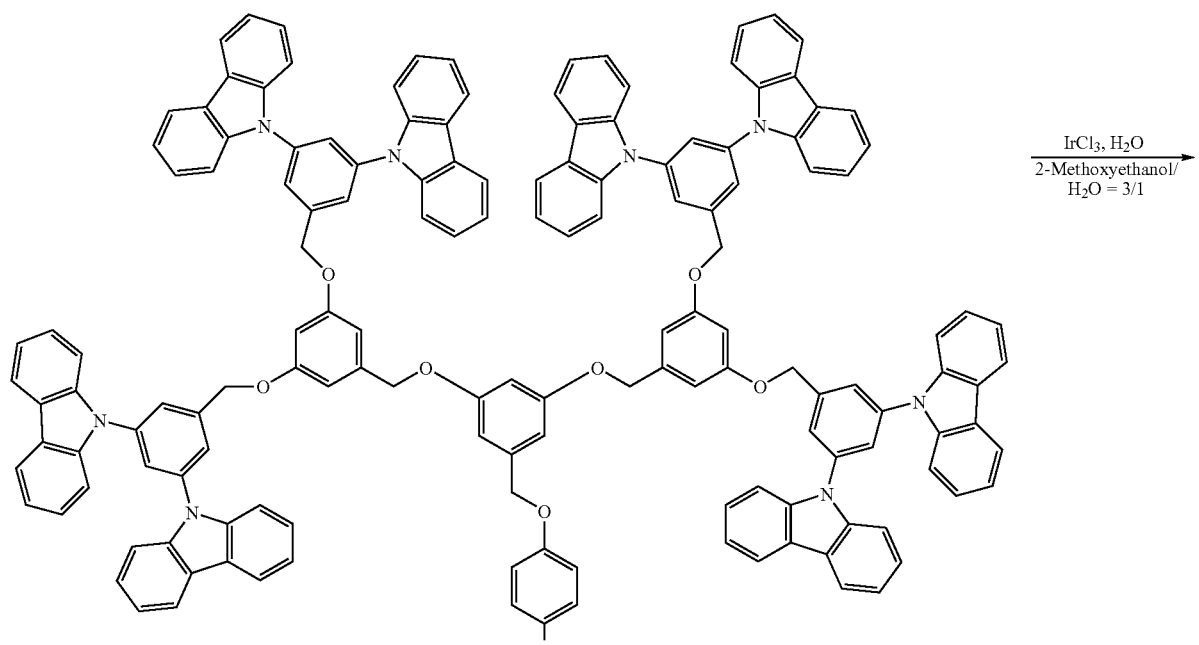
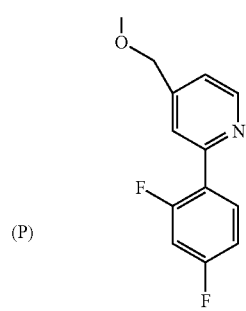
(P)

-continued
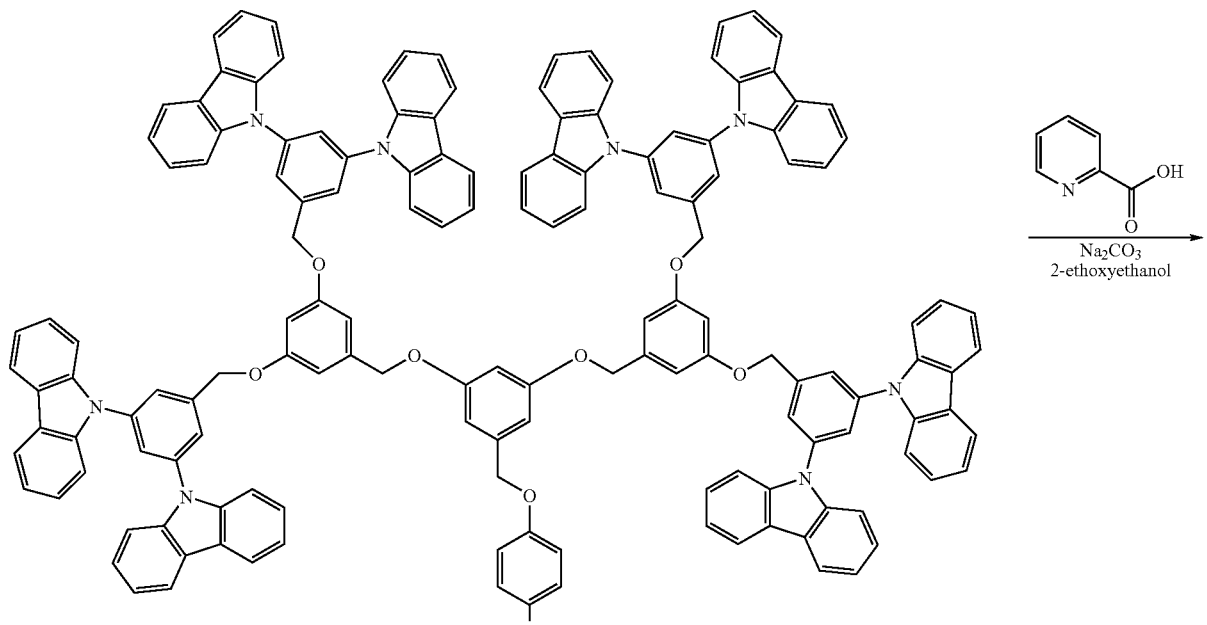
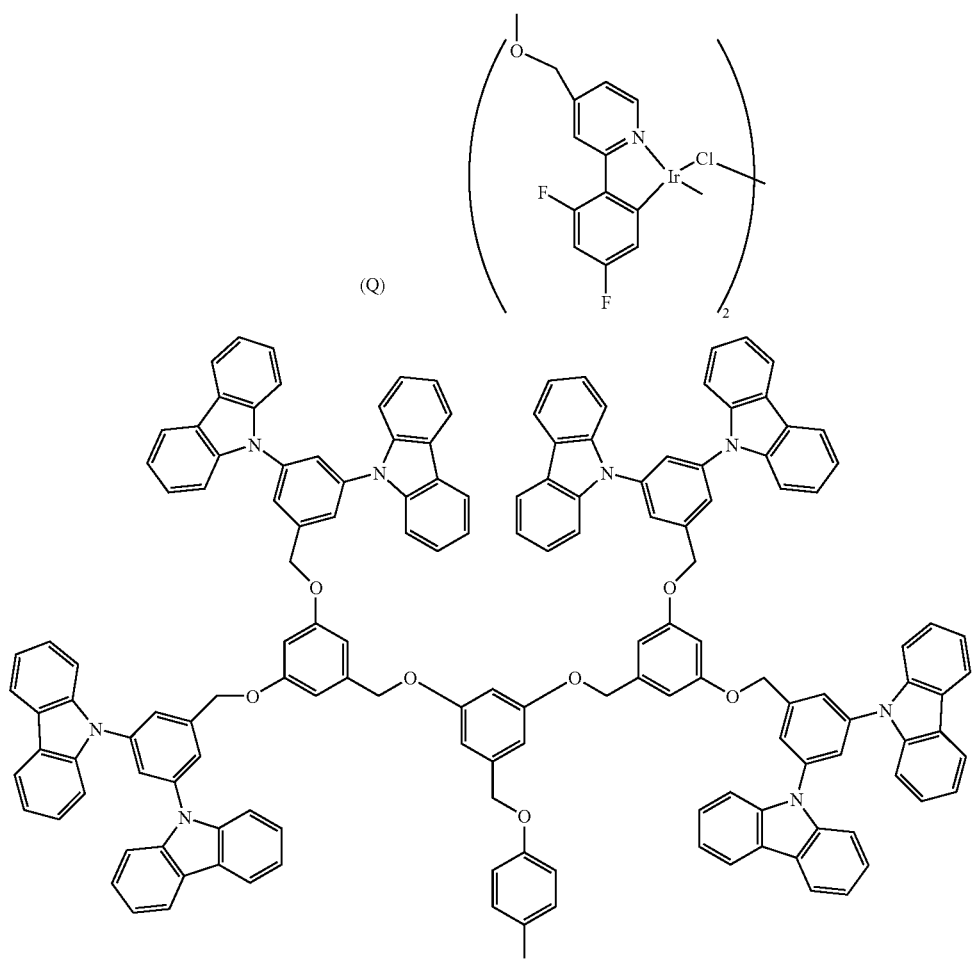

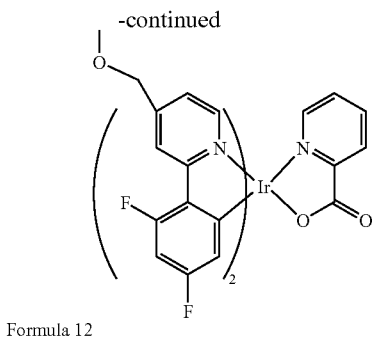

Formula 12

Synthesis of (M)

The compound (I) (0.5 mmol), 3,5-dihydroxybenzyl alcohol (0.25 mmol), $K_2CO_3$ (0.7 mmol), 18-crown-6 (0.05 mmol) and acetone (15 mL) were put together in a round bottom flask, followed by reflux at 50° C. for 10 hours. After confirming the reaction by TLC, the reaction mixture was filtered. The filtrate was washed with water and NaCl. The solvent was removed under high vacuum. The residue was purified with a fresh column to give solid compound (M). The yield was 95%.

The $^1$H-NMR$((CD_3)_2CO)$, 300 MHz spectrum results were as follows: d(ppm) 8.13(d, J=7.5, H=16), 7.83(s, H=8), 7.82(s, H=4), 7.51(d, J=8.1, H=16), 7.34(q, J=1.2, H=16), 7.21(t, J=7.5, H=16), 6.85(s, H=4), 6.83(s, H=2), 6.61(s, H=2), 6.17(s, H=1), 5.63(s, H=8), 5.00(s, H=4), 4.47(d, J=5.4, H=2)

Synthesis of (N)

The compound (M) (1 mmol) was put in a round bottom flask, to which $CH_2Cl_2$ (40 mL) was added. The temperature was lowered to 0° C. Phosphorous tribromide (1.2 mmol) was added thereto, followed by stirring for 3 hours. After confirming the reaction by TLC, the reaction mixture was washed with water and NaCl by using a separatory funnel. After eliminating the organic solvent, fresh column purification was performed to give solid compound (N). The yield was 80%.

Synthesis of (O)

The compound (N) (0.5 mmol), hydroquinone (1.5 mmol), cesium carbonate (1 mmol), and acetonitrile (50 mL) were put together in a round bottom flask. The reaction mixture was heat-stirred at 80° C. for 10 hours. After confirming the reaction by TLC, the reaction mixture was filtered. The filtrate was washed with water and NaCl. The solvent was removed under high vacuum. The residue was purified with a fresh column to give solid compound (O). The yield was 65%.

Synthesis of (P)

The compound (O) (0.1 mmol), the compound (B) (0.3 mmol), $K_2CO_3$ (0.15 mmol) and $CH_3CN$ (20 mL) were put together in a round bottom flask, followed by reflux at 80° C. for 10 hours. After confirming the reaction by TLC, impurities were eliminated by filtering. After washing with $CH_2Cl_2$, the filtrate was washed with water and NaCl. The solvent was removed under high vacuum. The residue was purified with a fresh column to give solid compound (P). The yield was 67%.

Synthesis of the Compound of Formula 12

Nitrogen was injected into 2-methoxyethanol (15 ml) at room temperature, followed by stirring for 30 minutes. Iridium chloride hydrochloride hydrate (0.04 mmol) and the compound (P) (0.08 mmol) were added thereto, followed by heat-stirring for 10 hours in the presence of nitrogen. After confirming the reaction by TLC, $H_2O$ was added to obtain a solid material. The product was filtered and then dried for 3 hours by vacuum pump to give compound (Q). The yield was 50%.

Nitrogen was injected into 2-ethoxyethanol (15 ml) at room temperature, followed by stirring for 30 minutes. The compound (Q) (0.05 mmol) and picolinic acid (0.15 mmol) were added thereto, together with $Na_2CO_3$ (0.5 mmol) as a base. The reaction mixture was heat-stirred for 5 hours in the presence of nitrogen, and the reaction was confirmed by TLC. The solvent was eliminated by distillation under reduced pressure, followed by extraction with methylene chloride. The extracted methylene chloride layer was washed with saturated NaCl solution, and then dried over $MgSO_4$. After removing the solvent by distillation under reduced pressure, the residue was added to hexane, resulting in a solid material. After filtering, the filtrate was purified by column chromatography, which was then dried for 3 hours by vacuum pump to give the compound of formula 12. The yield was 65%.

COMPARATIVE EXAMPLE 1

Synthesis of the Compound of Formula 14

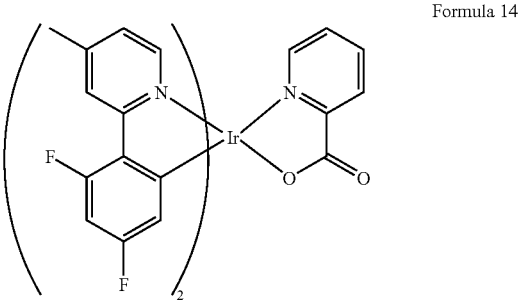

Formula 14

The compound of formula 14 used as a dopant was separately prepared. The compound can be synthesized by the conventional method or by the method described in Korean Patent Application No. 2003-87257.

COMPARATIVE EXAMPLE 2

Synthesis of the Compound of Formula 15

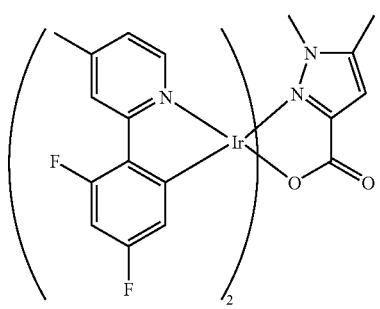

Formula 15

The compound of formula 15 used as a dopant was separately prepared. The compound can be synthesized by the conventional method or by the method described in Korean Patent Application No. 2003-79592.

EXPERIMENTAL EXAMPLE

The photoluminescence properties of the compounds of formula 6, 8, and 10, synthesized in Examples 1-3, were investigated. And the photoluminescence properties of compounds of formula 14 and 15, synthesized in Comparative Examples 1-2, were investigated for the comparison. The results are shown in FIGS. 1-6.

Figure 2:
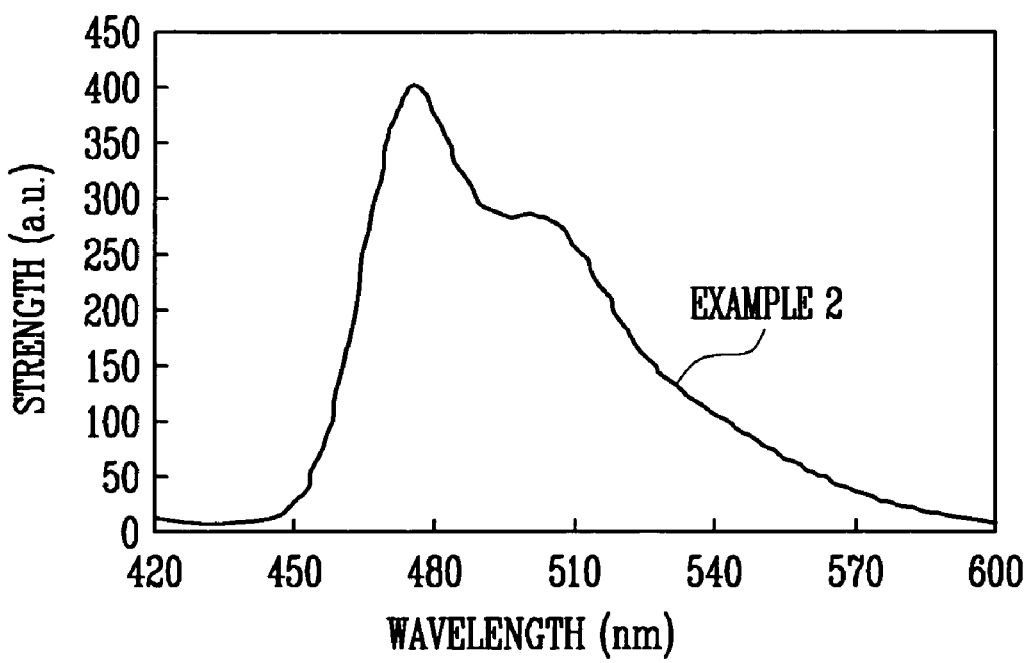
FIG. 2 is a graph showing a PL (photoluminescence) spectrum in chloroform solution of the compound represented by formula 8, synthesized in Example 2.
Figure 3:
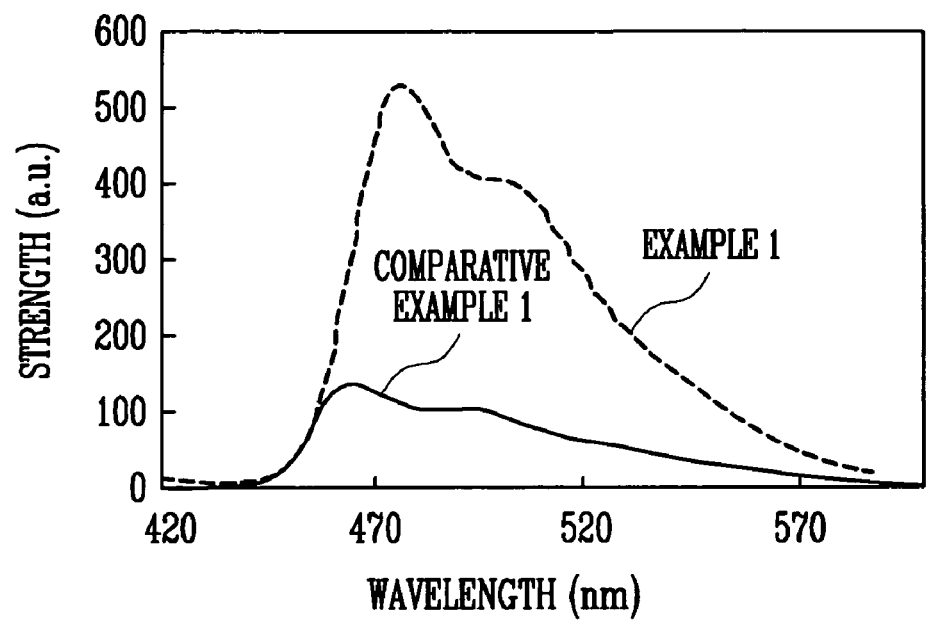
FIG. 3 is a graph showing the comparison of PL (photoluminescence) spectra in chloroform solution between the compound of Comparative Example 1 and the compound of Example 1.
Figure 4:
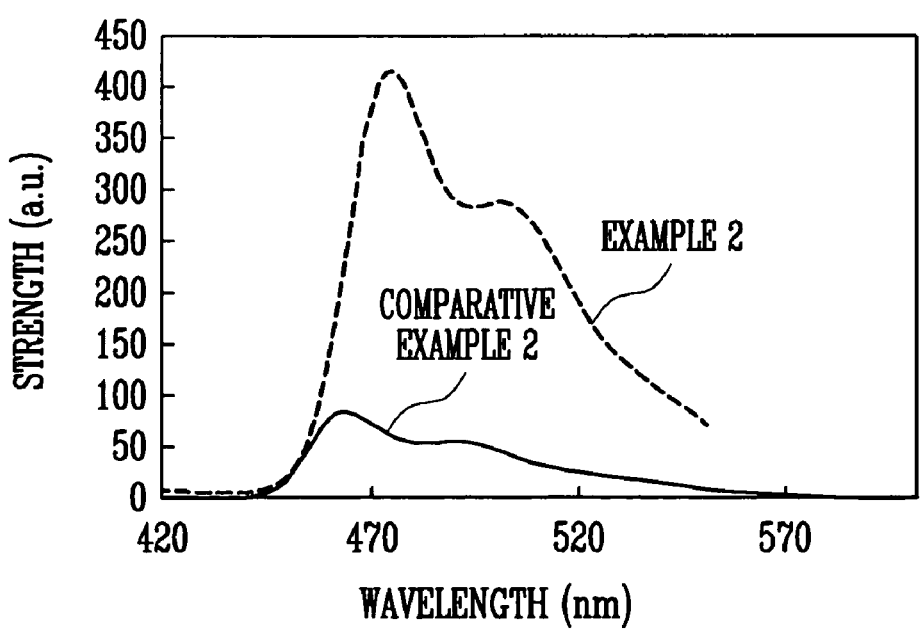
FIG. 4 is a graph showing the comparison of PL (photoluminescence) spectra in chloroform solution between the compound of Comparative Example 2 and the compound of Example 2.
Figure 5:
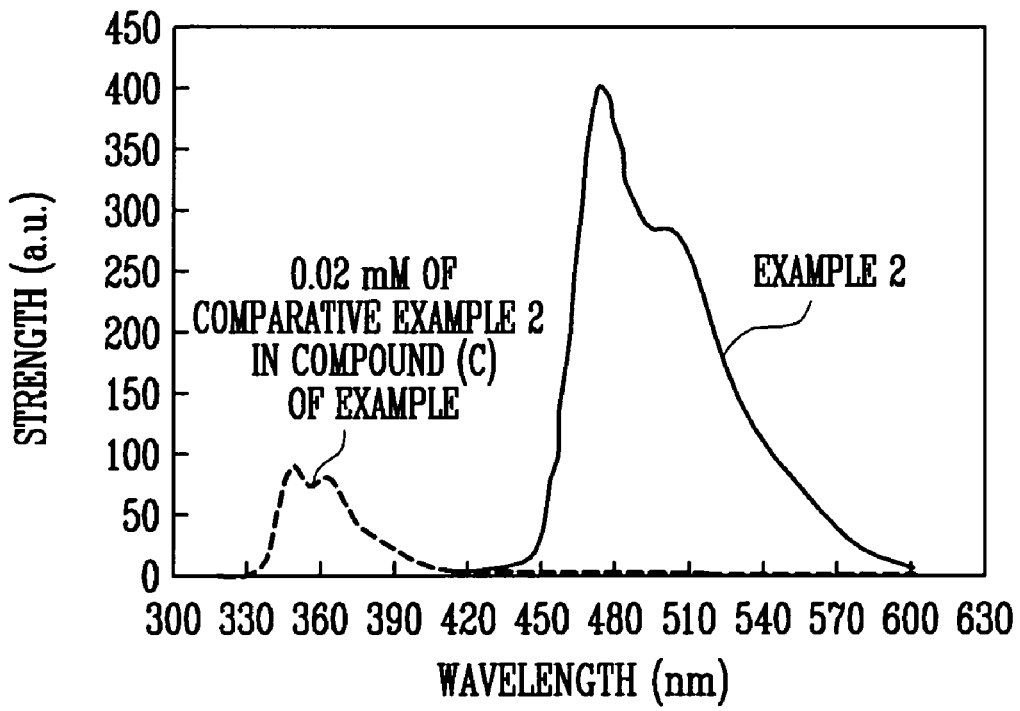
FIG. 5 is a graph showing the comparison of PL (photoluminescence) spectra in chloroform solution between organic metal compounds in which compounds for host and compounds for dopant are connected in one embodiment and a compound for host doped with 0.02 mM of compound for dopant.
Figure 6:
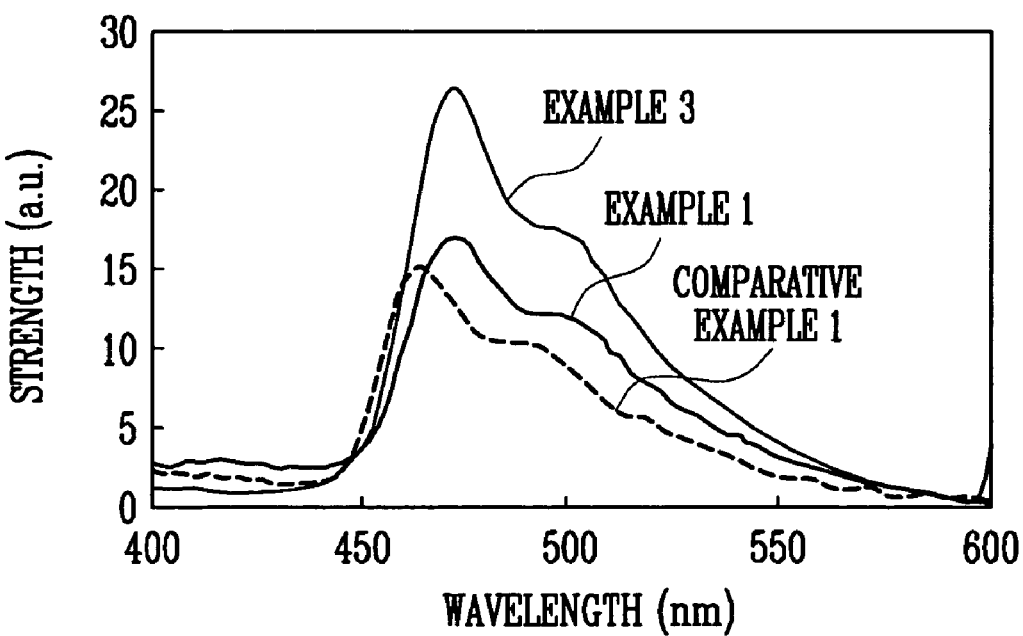
FIG. 6 is a graph showing the comparison of PL (photoluminescence) spectrums of PMMA (Poly(methyl methacrylate)) polymer films doped with compounds prepared in Example 1, Example 3 and Comparative Example 1, respectively.

FIG. 1 shows the photoluminescence (PL) spectrum in chloroform solution of the compound of formula 6 synthesized in Example 1, FIG. 2 shows the photoluminescence spectrum in chloroform solution of the compound of formula 8 synthesized in Example 2, FIG. 3 shows the comparison of photoluminescence spectra in 0.02 mM of chloroform solution of compounds respectively synthesized in Example 1 and Comparative Example 1, FIG. 4 shows the comparison of photoluminescence spectra in 0.02 mM of chloroform solution of compounds respectively synthesized in Example 2 and Comparative Example 2, FIG. 5 shows the comparison of photoluminescence spectra in 0.02 mM of chloroform solution between the compound of formula 8 synthesized in Example 2 in which compounds for host and compounds for dopant are connected each other and the compound(C) used for host doped with 33% level of compound for dopant represented by formula 15, FIG. 6 shows the photoluminescence spectra of PMMA polymer films pretreated with 90% PMMA and doped with 10% of Examples 1 and 3 and Comparative Example 1, respectively.

As shown in FIGS. 3, 4, and 6, the photoluminescence properties of the organic metal compound of the present embodiments in which the compounds for host were connected with the compounds for dopant were much greater than that of the compound for dopant itself. And as shown in FIG. 5, the photoluminescence properties of the organic metal compound of the present embodiments were also greater than those achieved when it was added respectively with the compounds for host and with the compounds for dopant.

Embodiment 1

For the anode, a $10\Omega/cm^2$ substrate provided by Corning Co. was used, and on top of the substrate, IDE 406 was vacuum-deposited to form a 600 Å thick hole injection layer. Next, on top of the hole injection layer, a TPD compound was vacuum-deposited to form a 300 Å thick hole transport layer. Upon completion of the formation of the hole transport layer, a 200 Å thick emitting layer was formed by 12% doping of the compound of formula 6 to CBP ((4,4'-N, N'-dicarbazole-biphenyl), on the top of the hole transport layer. Then, on top of the emitting layer, BCP (bathocuproine) was vacuum-deposited to form a 50 Å thick hole blocking layer. And on the upper part of it, Alq3 was vacuum-deposited to form a 200 Å thick electron transport layer. On top of the electron transport layer, LiF (10 Å thick) and Al (3000 Å thick) were serially vacuum-deposited, resulting in the generation of a LiF/Al electrode. As a result, an organic electroluminescence device was prepared.

Efficiency, driving voltage, color purity and lifetime of the organic electroluminescence device prepared in Embodiment 1 were investigated. As a result, the organic electroluminescence device of the present embodiments was proven to have excellent efficiency, driving voltage, color purity, and lifetime.

The effects of the present embodiments are as follows.

First, the organic metal compound of the present embodiments can be effectively used as a coloring material of photoluminescence devices since it has a low molecular level emitting property.

Second, the organic metal compound of the present embodiments has a structure having the connection of the compounds for host and the compounds for dopant, so that its solubility can be remarkably increased owing to the increased molecular weight (even though each compound has low molecular weight, when they are connected with each other to form a compound, the resultant compound becomes high molecular one). Thus, a wet process such as spin coating can be applied for the preparation of the device.

Third, the photoluminescence device prepared by using the organic metal compound of the present embodiments has enhanced efficiency, driving voltage, color purity and life-

What is claimed is:

1. An organic metal compound having the following structure:

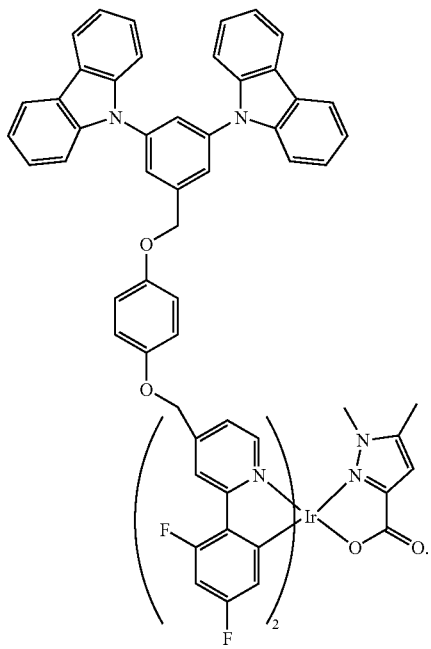

2. An organic metal compound having the following structure:

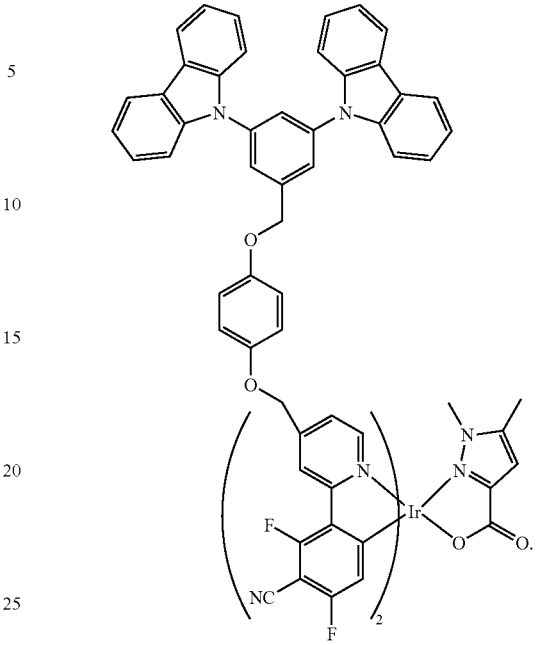

3. An organic electroluminescence device comprising an organic layer in between a pair of electrodes, wherein the organic layer contains the organic metal compound of claims 1 or 2.

4. The organic electroluminescence device as set forth in claim 3, wherein the organic layer is an emitting layer.

5. A preparation method for an organic electroluminescence device comprising the following steps:
   forming a first electrode on a substrate;
   forming an organic layer on the first electrode;
   and forming a second electrode on the organic layer, wherein the organic later is formed by doping the organic metal compound of claims 1 or 2.

6. The preparation method for an organic electroluminescence device as set forth in claim 5, wherein the first electrode is an anode, the second electrode is a cathode, and the organic layer is an emitting layer.

7. The preparation method of the organic electroluminescence device as set forth in claim 5, wherein the organic layer is formed by a wet process.

* * * * *